United States Patent [19]

Bai

[11] Patent Number: 4,619,643
[45] Date of Patent: Oct. 28, 1986

[54] CATHETER

[76] Inventor: Chao-Liang Bai, 1294 Islington Ave., Apt. 404, Toronto, Ontario M9A 3K2, Canada

[21] Appl. No.: 621,482
[22] Filed: Jun. 18, 1984

[30] Foreign Application Priority Data

Jul. 25, 1983 [CA] Canada ................................. 433088

[51] Int. Cl.⁴ .............................................. A61M 5/00
[52] U.S. Cl. ...................................... 604/43; 604/164
[58] Field of Search ...................... 604/27, 39, 43, 144, 604/45, 93, 164, 280, 4

[56] References Cited

U.S. PATENT DOCUMENTS

| D. 272,651 | 2/1984 | Mahurkar | 604/44 X |
|---|---|---|---|
| 883,583 | 3/1906 | Stallsmith | 604/43 |
| 1,696,018 | 12/1928 | Scherberg | 604/39 |
| 2,230,218 | 2/1941 | Asche | 604/43 |
| 4,016,879 | 4/1977 | Mellor | 604/44 X |
| 4,037,599 | 7/1977 | Raulerson | 604/44 |
| 4,073,297 | 2/1978 | Kopp | 604/44 |
| 4,098,275 | 7/1978 | Consalvo | 604/27 X |
| 4,253,463 | 3/1981 | Kim | 604/164 X |
| 4,493,696 | 1/1985 | Uldall | 604/164 X |

FOREIGN PATENT DOCUMENTS 50089 8/1982 Canada .

Primary Examiner—Stephen C. Pellegrino
Attorney, Agent, or Firm—Bachman & LaPointe

[57] ABSTRACT

A double lumen catheter made up of an elongated integral flexible plastic thin-walled tubular body extending from a proximal end part, through an intermediate part, to a distal end part, terminating in a tip. The intermediate part has an outer wall and an internal septum wall containing juxtaposed arterial and venous lumens. The terminal end of each lumen in the proximal part is adapted for connection to an access tube to hemodialysis apparatus. At the junction of the intermediate part and the distal part, the arterial lumen is terminated and the venous lumen continued at least part way to the tip of the distal part. The outside surface of the outer walls are continuous and smooth to offer minimum resistance to insertion into the body of a patient. The walls are also relatively thin to provide for lumens of relatively large cross-section compared to the total cross-section of the catheter body. Removable obturators are inserted in the lumens to prevent the catheter from buckling. The inner surface of the outer walls and the surfaces of the septum wall are continuous and smooth and any change of direction in the lumen wall is in a gradual curve to accommodate negotiation by a flexible obturator. Alternatively, the catheter may be made from tubing sufficiently resistant in itself to buckling for the catheter to be inserted without the use of obturators. One such form of tubing is made of alternating hard and soft plastic rings welded together. Another form employs wire reinforcing within the walls. Welding and molding methods for making the catheters are disclosed.

18 Claims, 103 Drawing Figures

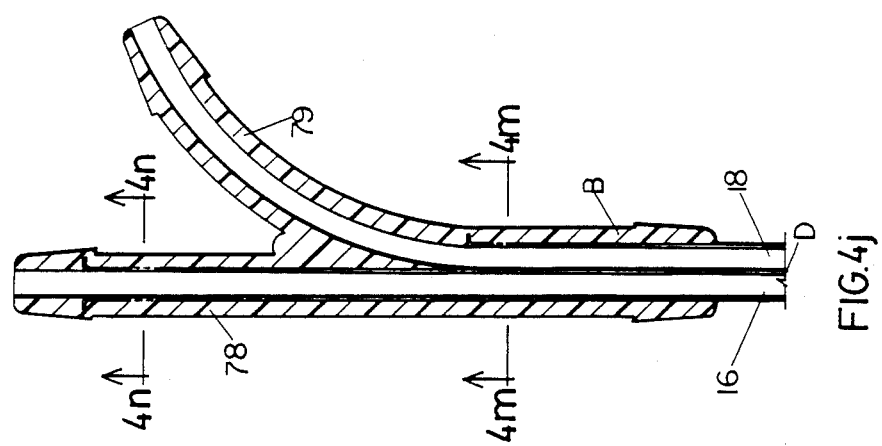
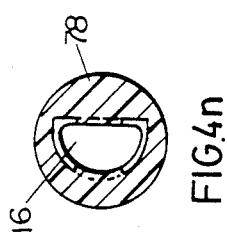
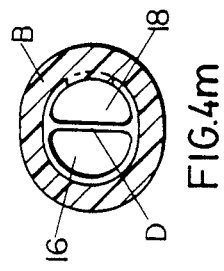
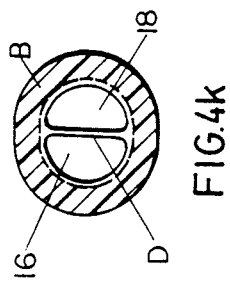
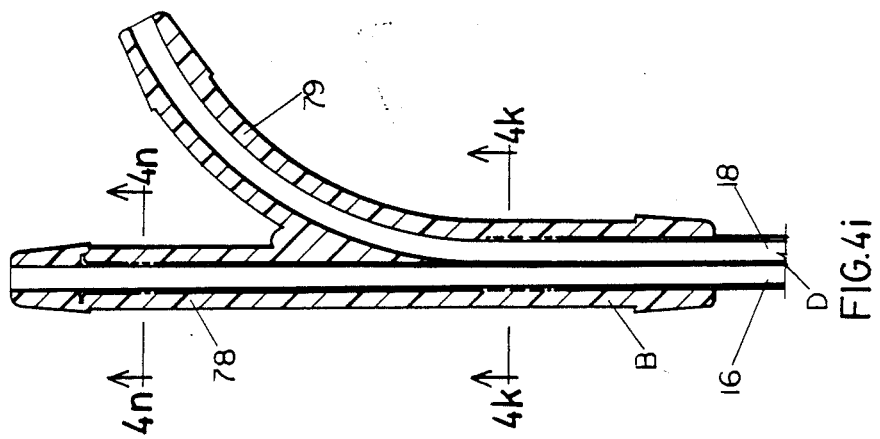

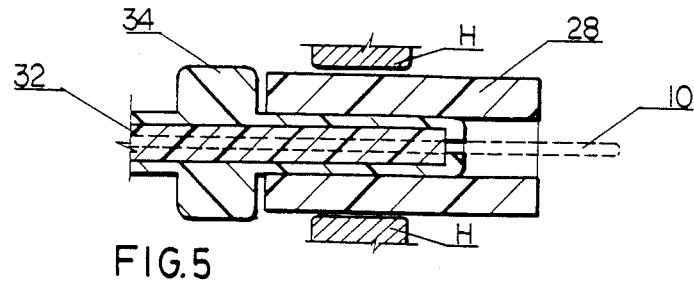
FIG.5
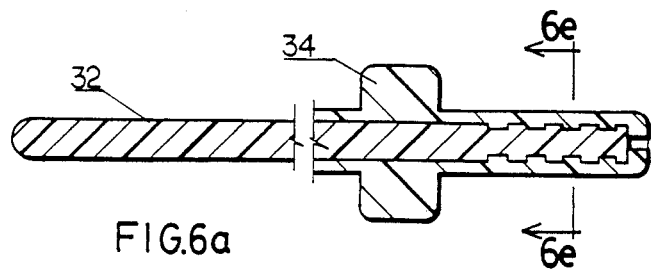 
FIG.6a  FIG.6e
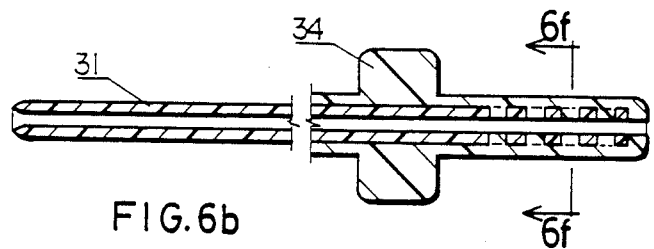 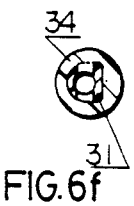
FIG.6b  FIG.6f
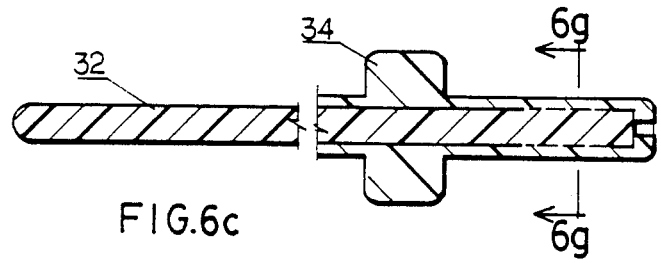 
FIG.6c  FIG.6g
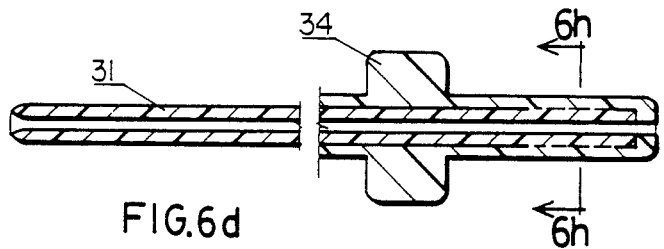 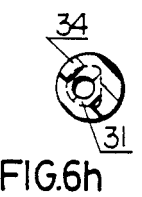
FIG.6d  FIG.6h

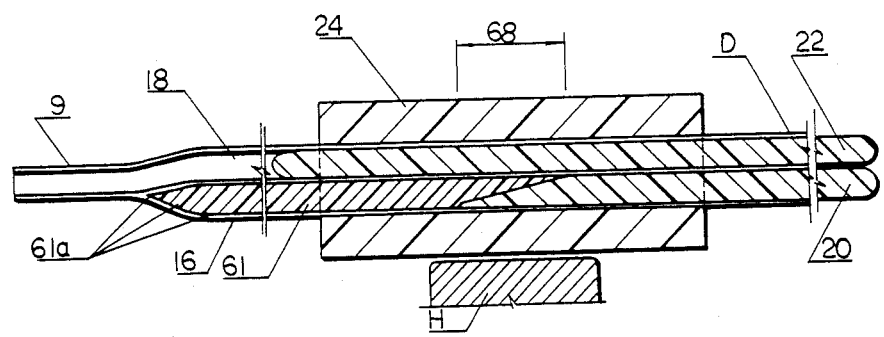
FIG.18
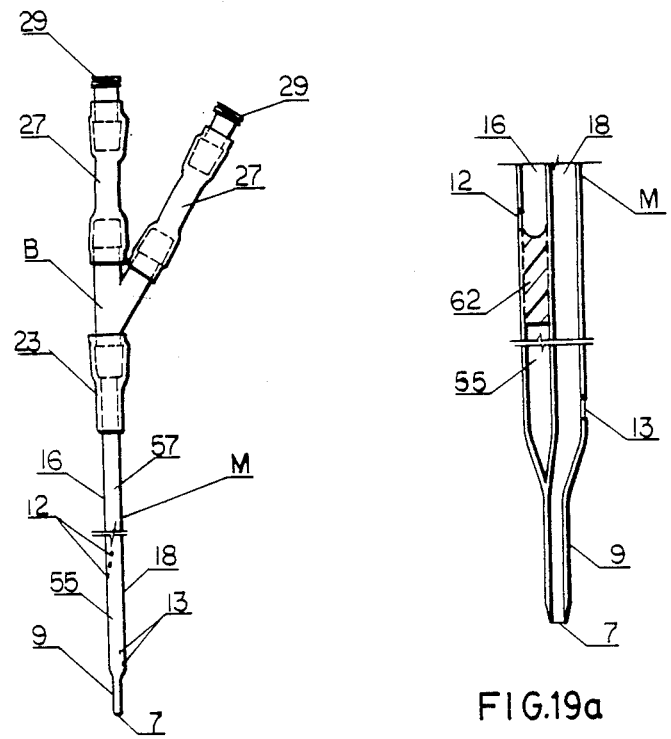
FIG.19
FIG.19a

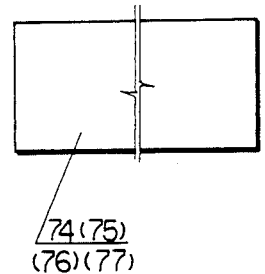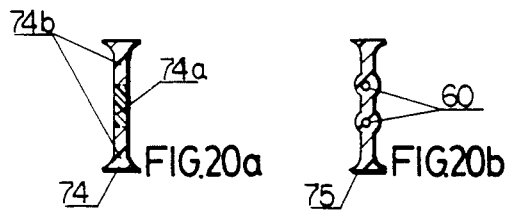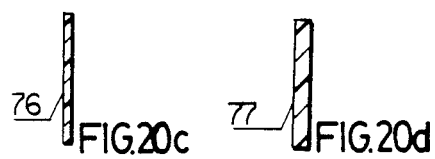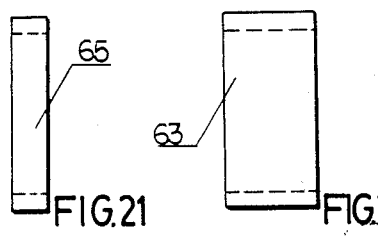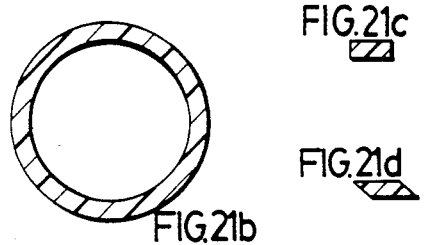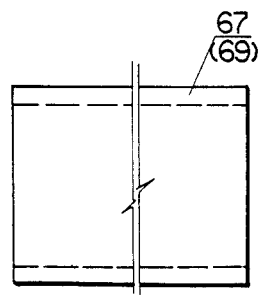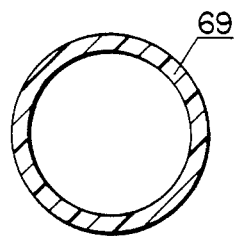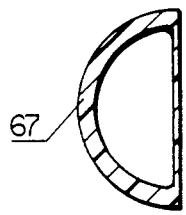

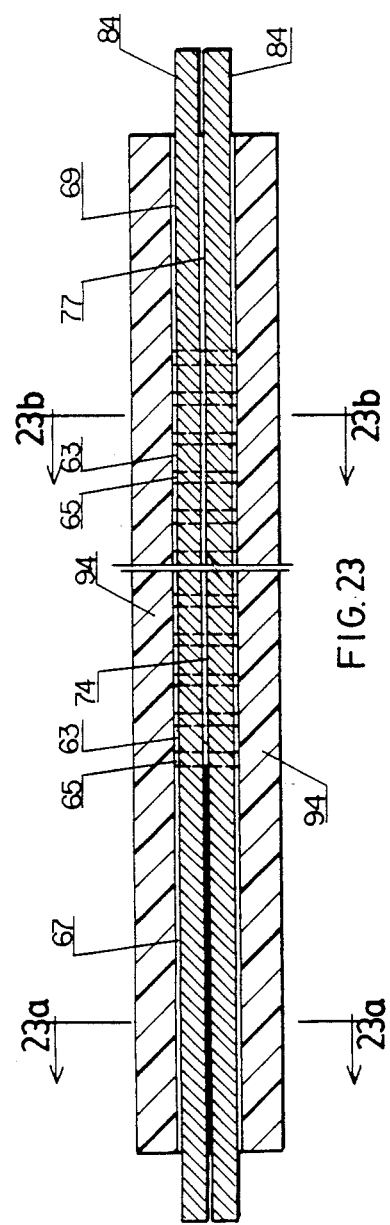
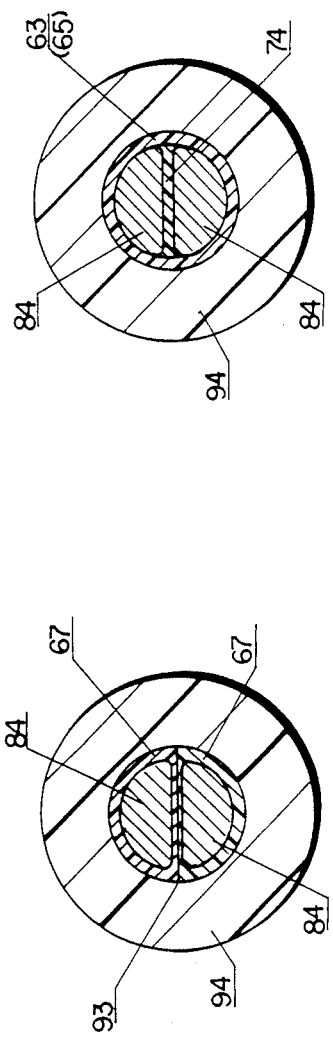
FIG.23
FIG.23b
FIG.23a

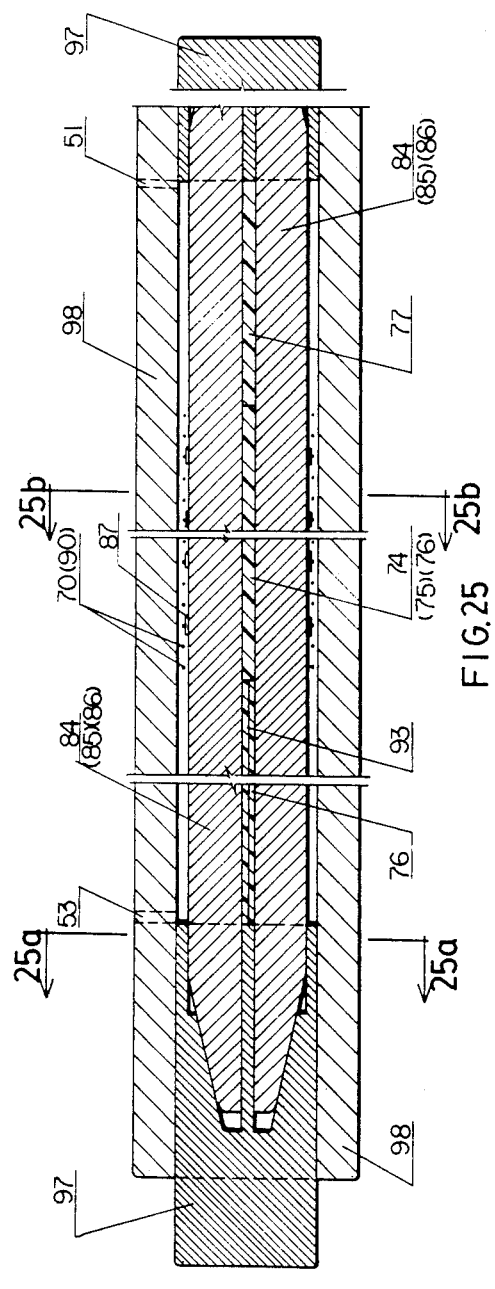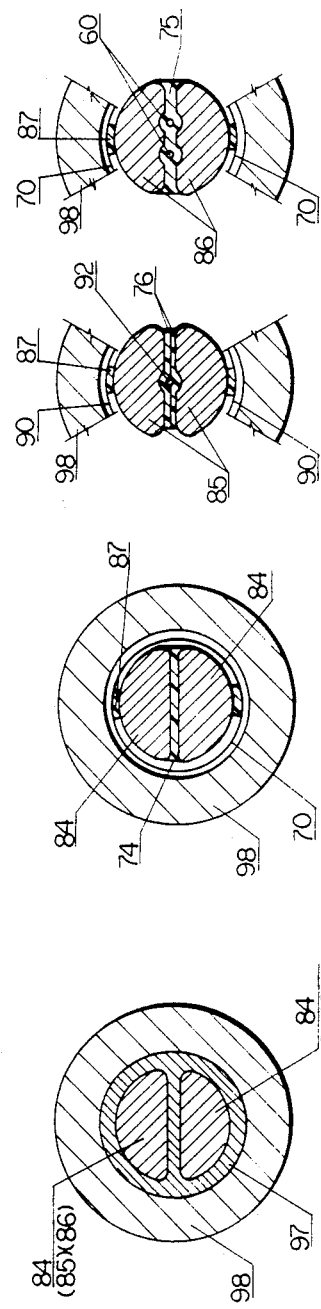

CATHETER

BACKGROUND OF THE INVENTION (1) Field of the Invention

This invention relates to catheters made of plastic material for gaining temporary vascular access to the circulatory system of a patient requiring hemodialysis.

More specifically, such a catheter is designed to catheterize a predetermined blood vessel of a patient by a single puncture. The catheter is inserted into the blood vessel so that untreated blood is withdrawn continuously from that vessel and passed to a dialysis apparatus. Processed blood is returned from the apparatus to the same blood vessel.

(2) Description of the Prior Art

It is well accepted medical practice in the performance of both emergency and chronic hemodialysis to use a double lumen catheter of concentrically disposed tubular construction. See, for example, FIG. 5 in Raulerson, U.S. Pat. No. 4,037,599, and FIGS. 3, 4 and 5 in Allentyne Limited, Canadian Pat. No. 1,092,927.

The placement of catheters of this type is accomplished commonly by the "Seldinger" technique. This technique involves the puncture of a vein with a hollow needle. A flexible stainless steel wire is then threaded through the needle and into the vein. The needle is withdrawn over the wire and the flexible plastic catheter slipped down over the wire, as a guide for proper placement of the distal end of the catheter inside the blood vessel. A typical subclavian application of a double lumen catheter is shown in Canadian Pat. No. 1,092,927.

It can be seen that once the catheter is inserted into the vein of a patient, it serves as a linkage between the blood stream and an extracorporeal hemodialysis circuit. The arterial lumen of the catheter captures, from the vein, the arterial blood to be treated and the venous lumen returns fresh or processed blood (venous flow) into the same vein downstream of the blood flow. This arrangement makes the extracorporeal hemodialysis circuit, including the catheter, in effect, an extension of the patient's vein.

There must be an opening at the distal tip of the catheter large enough to receive a guidewire. The surface surrounding this opening must be rounded and smooth and the diameter of the body of the catheter must increase gradually and smoothly to ease its insertion.

Even though dialysis may only be performed intermittently, it is common to leave the catheter in the patient's vein for some time, say up to about two weeks, and between dialysis to inject into the catheter a drug to prevent blood clotting, for instance heparin. It is desirable that the drug remain in the catheter for as long as possible.

A major problem in catheterizing is kinking of the catheter during insertion. One attempt to overcome this has been to employ, in the outer tube of a concentric double lumen catheter, relatively heavy tubing, for example, of Teflon, and to rely on the wall thickness to prevent kinking. While the thicker tubing impedes insertion, it has not been altogether effective to prevent kinking and a proportion of catheters made in this way still kink.

Another problem with the concentric tubular construction is that, despite the size of the tubing, the lumen does not allow adequate blood flow, because of the significant thickness of the wall compared to the overall diameter and the significant cross-sectional area of the inner tubing.

A still further problem is that there is dead space in the Y-adapter commonly forming a part of the catheter causing disorder of the blood flow. Blood clotting also takes place more frequently with double lumen catheters than with single lumen catheters.

An aim of the present invention is to provide catheters and methods of making them which overcome these problems and which provide positive advantages as will be apparent from the detailed description to follow.

SUMMARY OF THE INVENTION

Having regard to what has been said, a double lumen catheter, according to one preferred form of the invention, comprises a thin septum-walled double lumen plastic tubing body and a removable obturator extending within each lumen when the catheter is inserted.

The use of obturators, extending within both lumens of a suitably constructed catheter, provides lateral support to the wall of the tubing throughout its length. This prevents it from buckling inward and kinking under the eccentric axial load encountered during the insertion into the body.

The catheter is constructed to facilitate the insertion and removal of obturators and, at the same time, obviate the problem of oversized tubing, restricted patency, dead space, and blood clotting.

The invention also contemplates novel septum-walled double lumen tubing having unique cross-sections and novel branched adapters.

A preferred catheter is made up of an elongated integral flexible plastic thin-walled tubular body extending from a proximal end part, through an intermediate part, to a distal end part, terminating in a tip. The intermediate part has an outer wall and an internal septum wall containing juxtaposed arterial and venous lumens. The proximal end part is a continuation of the intermediate part and either continues in juxtaposed lumens or, preferably, is branched to provide diverging lumens. The end of each lumen, in the proximal part, is adapted for connection to an access tube, leading to hemodialysis apparatus. At the junction of the intermediate part and the distal part, the arterial lumen is terminated and the venous lumen continued at least part way to the tip of the distal part. The cross-section of the lumens in the intermediate part is uniform throughout, although the cross-section of the lumens in the proximal part may be the same or slightly larger than in the intermediate part. The venous lumen continues at the same cross-section, or slightly less, throughout at least one obturator-receiving length of the distal part.

The outside surface of the outer walls are continuous and smooth so as to offer minimum resistance to insertion into the body of a patient. The walls are also relatively thin to provide for lumens of relatively large cross-section compared to the total cross-section of the catheter body. This particular form of the device employs removable obturators to prevent the catheter from buckling while it is being inserted. The overall construction of the body is designed to receive an obturator in each lumen land to facilitate their insertion and withdrawal. So, the inner surface of the outer wall and the surfaces of the septum walls are continuous and smooth and any change of direction, for example, between the intermediate and proximal or distal end parts in the lumen, as in some embodiments, is a gradual curve to accommodate its negotiation by a flexible obturator.

The obturator for the arterial lumen is solid and that for the venous lumen has a passage extending through it to accommodate a wire used with a needle to insert the catheter into the body of the patient.

The ability to fashion an effective thin-walled body is facilitated by the use, in preferred embodiments, of plastic tubing having a special cross-sectional shape. This cross-sectional shape may be symmetrical, for example, somewhat oval with a long and short axis, the septum wall being in the short axis and the lumens being of the same cross-section. Variations of this shape are shown in the drawings. Or, the shape may be non-symmetrical, with the respective lumens of the same cross-sectional area, but of different shape. One of the lumens could be larger than the other, if desired, but the septum wall should be parallel to the short axis.

The proximal end of the catheter may also assume different forms, for example, it may be straight or branched, the proximal end of the body diverges into branches, each enclosing the continuation of a lumen from the intermediate part. Desirably, the branched proximal end of a catheter is contained in and firmly fixed to a branched adapter. In one version, the adapter is molded integrally with the proximal end of the tubing. In another form, the branched adapter and the proximal end are formed separately, but later permanently connected by welding.

The distal end part of the catheter may vary in different respects. In all forms, there is a narrow leading end part, extending from the intermediate part to a tip, which accommodates part of the venous lumen. In one case, this leading end part is connected to the intermediate part by a tubular extension of the intermediate part which is of large enough cross-section to receive the venous lumen obturator. This extension may be aligned with the venous lumen in the intermediate part or may be smoothly offset inwards to be axially aligned with the intermediate part. Another construction lacks the narrow leading end part and the distal part terminates with the extension, which is itself provided with a tip opening of the same diameter as that of the venous lumen so as to allow the venous lumen obturator to protrude in an insertable tip.

In still further forms of distal part, the leading end part is made up of an extension of the same diameter as the intermediate part which ultimately tapers symmetrically to provide the leading end part. In this case, the arterial lumen extends part way into the distal end part and the extension is filled with a plug so as to terminate the effective length of the arterial lumen near the beginning of the distal part. In all cases, there is a blood-conducting orifice through the outside wall of the catheter in the distal end part, leading to the arterial lumen.

The invention also contemplates special forms of obturators as will be apparent from the description to follow.

The invention also contemplates other ways of making the catheter body rigid enough to insert into the body of a patient without the use of obturators. One way of doing this is by employing unique tubing made up of a series of alternating hard and soft plastic rings welded together. The hard plastic rings should be at least twice the length of the soft plastic rings. The septum wall is welded within the tubing to divide it into respective lumens.

Another form of special tubing which may be employed is wire-reinforced. One embodiment has a continuous wire as a spiral within the wall of the tubing and looping back at the distal end.

Another type of tubing has a septum wall, incorporating length-stabilizing means, for example, the septum wall has a central part of hard, but flexible plastic, and side parts of soft elastic plastic welded to the central part and to the outer wall.

In still another form, the length of the tubing is stabilized by providing a septum wall of soft elastic plastic with a wire extending through it in both directions and looping back at the distal end.

While certain forms of catheter have been described as not needing obturators, obturators could be employed with these catheters as well, if desired.

The catheters described are fashioned by the use of particular welding and molding techniques, described herein in detail and which form part of the invention.

BRIEF DESCRIPTION OF THE DRAWINGS

Having thus generally described the invention, it will be referred to more specifically by reference to the accompanying drawings, which illustrate preferred embodiments, and in which:

FIGS. 2a to 2f are transverse cross-sections on a still further enlarged scale through several different types of tubing suitable for use in a catheter body of the type shown in the previous Figs.;

FIGS. 2g to 2s are transverse cross-sections on the scale of FIGS. 2a to 2f through obturators for use in the lumens of catheter bodies shown beside them in the drawings;

FIGS. 4b, 4i and 4j show three alternate forms of proximal end part of a catheter according to the invention;

FIGS. 4d to 4h and 4k to 4n are transverse cross-sections along the lines shown in FIGS. 4a, 4b, 4c, 4i and 4j (FIGS. 4d, 4e and 4f appear on the sheet with FIG. 4a and FIGS. 4g and 4h are on the sheet with FIGS. 4b and 4c);

FIG. 5 illustrates a step in the manufacture of an obturator, according to the invention;

FIGS. 6a to 6d are enlarged fragmentary longitudinal cross-sections through different forms of obturator;

FIGS. 6e to 6h are transverse cross-sections through the obturators of FIGS. 6a to 6d;

FIGS. 15, 15a, 15b, 16, 17a to 17d and 18 are fragmentary cross-sectional views showing different ways of fashioning the distal end of the catheter as shown in FIGS. 1a to 1e;

FIG. 19 is a general view in side elevation of a further form of catheter, according to the invention;

FIG. 19a is an enlarged fragmentary longitudinal cross-section through the distal end of the catheter of FIG. 19;

FIG. 20 is a side elevation of the septum wall of the tubing shown in cross-section in FIGS. 27 and 28;

FIGS. 20a to 20d are transverse cross-sections through different types of septum wall of the general type shown in FIG. 20;

FIG. 21 is a side elevation of a ring of soft plastic used as a component in making multi-ring tubing;

FIG. 21a is a side elevation of a ring of hard plastic used in combination with the soft plastic ring of FIG. 21 to make the tubing;

FIG. 21b is a transverse cross-section of the rings of FIGS. 21 and 21a;

FIGS. 21c and 21d show alternative cross-sectional shapes for the wall of the ring shown in FIG. 21b;

FIG. 22 is a side elevation of another form of tubing made of soft plastic shown in cross-section in FIGS. 22a and 22b;

FIG. 22a is a cross-section through the tubing of FIG. 22;

FIG. 22b is a cross-section through another kind of tubing similar to that of FIG. 22;

FIG. 23 is a longitudinal cross-section illustrating an assembly in the manufacture of multi-ring tubing, according to the invention;

FIGS. 23a and 23b are transverse cross-sections through the assembly of FIG. 23;

FIG. 25 is a longitudinal cross-section illustrating an assembly in the manufacture of metal-spring tubing, according to the invention;

FIG. 25a is a cross-section as along the line 25a—25a of FIGS. 25 and 26;

FIG. 25b is a cross-section as along the line 25b—25b of FIGS. 25 and 26;

FIG. 25c is a cross-section as along the line 25b—25b of FIGS. 25 and 26 through another type of tubing, the septum wall differing from that of FIG. 25b;

FIG. 25d is a cross-section as along the line 25b—25b of another form of catheter body in which the septum wall differs from that of FIGS. 25b and 25c;

FIG. 28b is a transverse cross-section through a slightly modified form of tubing to that of FIG. 28a.

DESCRIPTION OF THE PREFERRED EMBODIMENTS

General Construction

Figure 1:
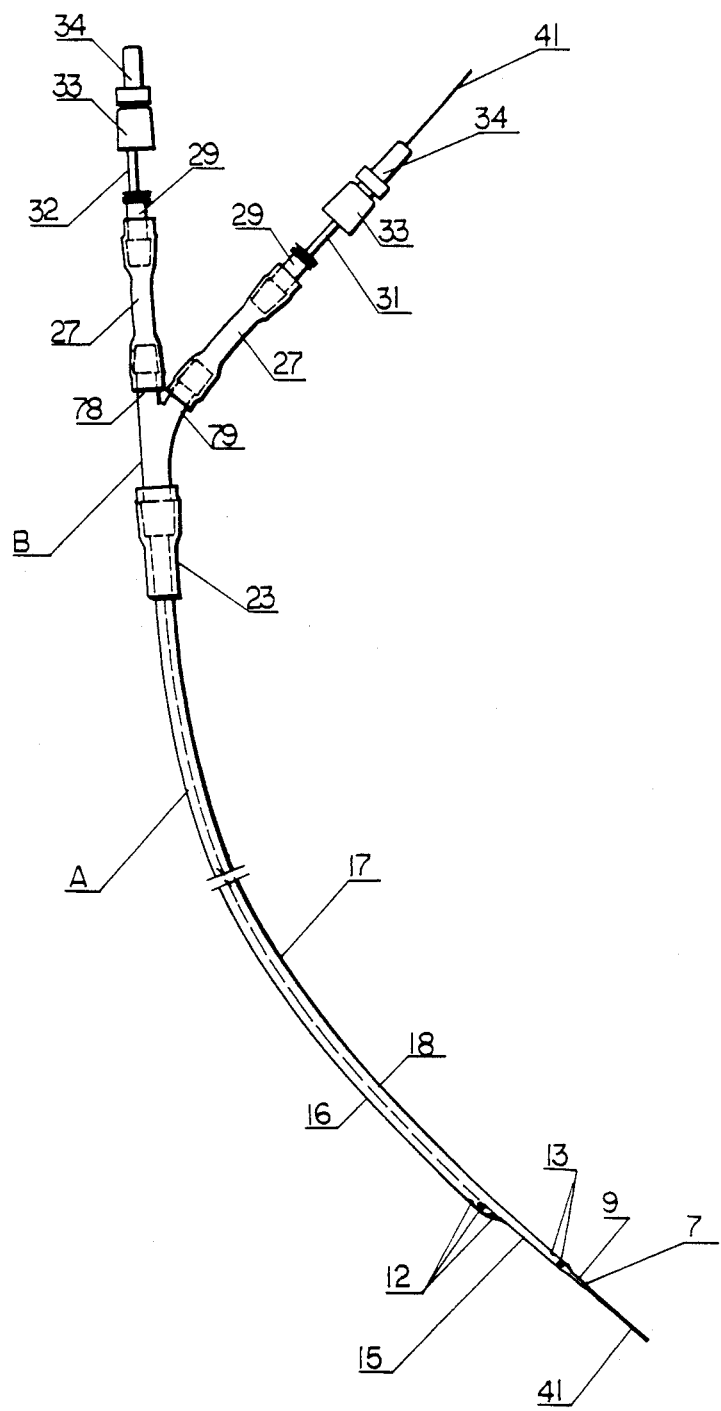
FIG. 1 is a general view in side elevation of a catheter, according to the invention.

FIG. 1 is a side elevation of a catheter, according to the invention, with obturators and guidewire in place, in a condition ready for insertion into a vein of a patient once the luer locks 33, 29 are closed.

The catheter is made up of an integral elongated septum-walled double-lumen body A of thin tubular plastic material having outer walls and a septum wall providing a venous lumen 18 and an arterial lumen 16 juxtaposed to it.

Figures 2A, 2G, 2M:
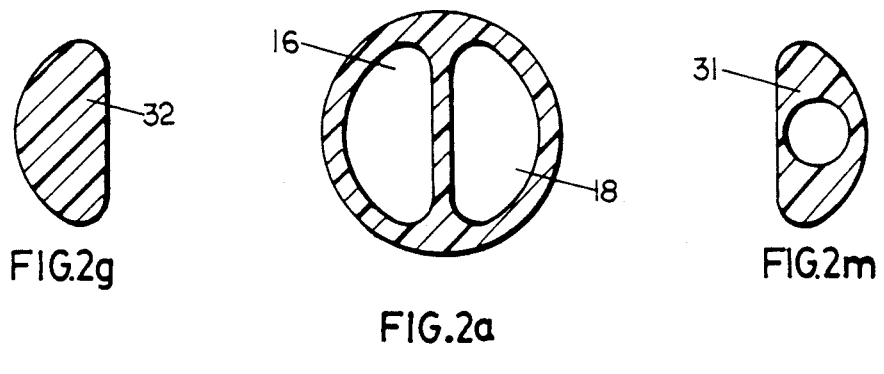
Figures 2B, 2H, 2N:
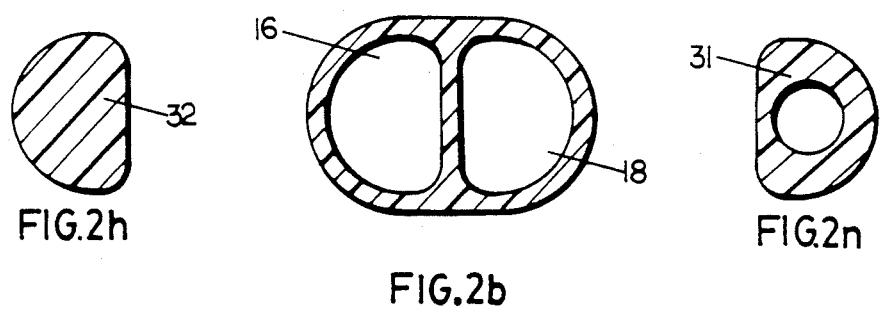
Figures 2C, 2I, 2P:
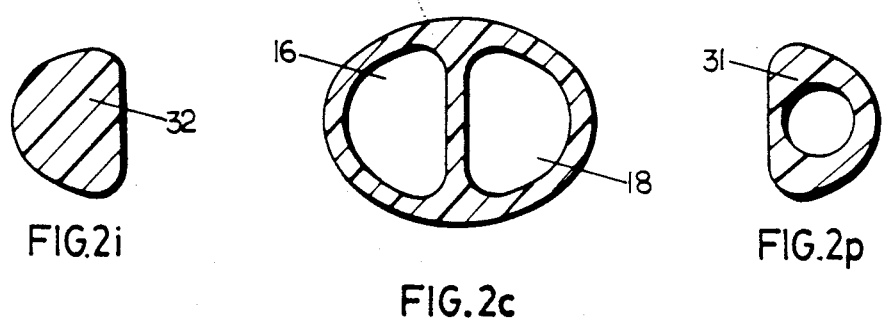
Figure 2J:
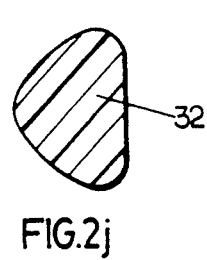
Figure 2D:
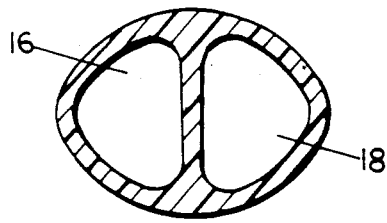
Figure 2Q:
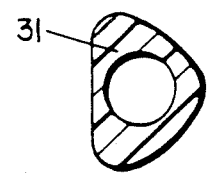
Figure 2K:
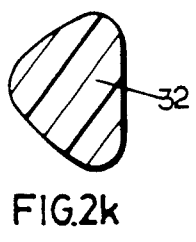
Figure 2E:
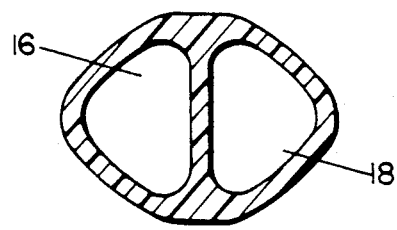
Figure 2R:
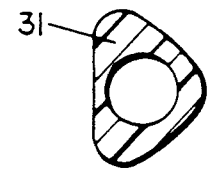
Figure 2L:
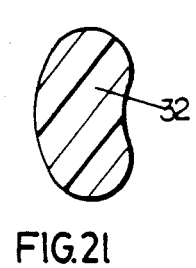
Figure 2F:
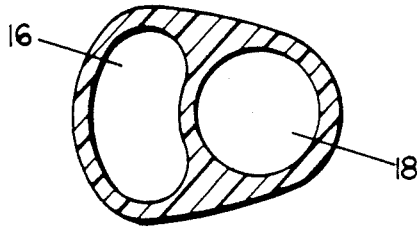
Figure 2S:
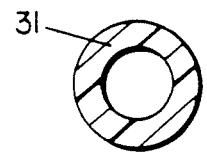
Figure 3A:
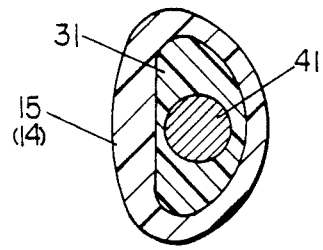
FIGS. 3a to 3f are transverse cross-sections on the scale of FIGS. 2a to 2f through a distal part of various catheters as shown in FIGS. 2a to 2f with obturator and guidewire in place.
Figure 3D:
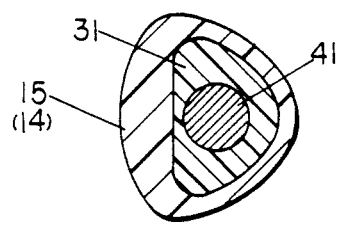
Figure 3B:
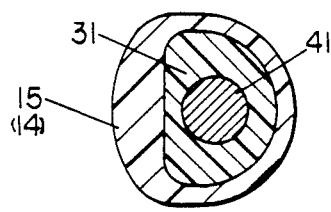
Figure 3E:
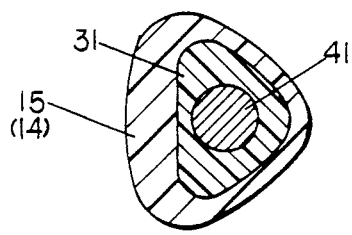
Figure 3C:
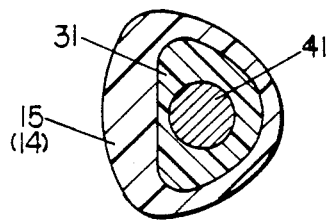
Figure 3F:
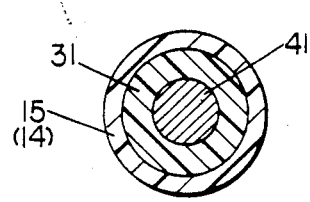

The cross-section of the body A may be circular (FIG. 2a), flat circular (FIG. 2b), elliptical (FIGS. 2c and 2d), rhomboid with arcuate sides (FIG. 2e) or oval (FIG. 2f).

The body A extends from a distal end part 15, through an intermediate part 17, to a proximal end part. At the distal end part 15, there is only one lumen 18 (a venous lumen) whose cross-section is shown, in alternative form it may take in FIGS. 3a, 3b, 3c, 3d, 3e and 3f with a tapered tip 9 and an end hole 7.

There are also two groups of side holes (preferably 0.040 inches to 0.045 inches in diameter). These holes are preferably arranged spirally. One group 12 of side holes is on the end of the lumen 16 as a blood inlet. Another group 13 is on the end of the luemn 18 as a blood outlet.

Modifications of the distal end part 15 are shown in FIGS. 1a, 1b, 1c, 1d and 1e. At the proximal end part, two lumens of the body A are separated into two branches 19 and 21, the branches and part of the body A being contained and fixed within a branched adapter B, in this case a Y-adapter. The intermediate part 17 is curved to match the shape of the vein so that after the catheter is inserted there is almost no bending stress on the body of the catheter.

The body A is made up of tubing D which will be described below under "Manufacturing Procedure".

A tube 23 of silicon elastomer surrounds the proximal end of the body A and the end of the Y-adapter B.

A silicon elastomer tube 27 connected to the end of each branch of the Y-adapter B to a female luer lock 29 which, in turn, engages a male luer lock having a body 34 and a cap 33. The body 34 of one male luer lock engages an obturator 31, the other an obturator 32 (the end of an obturator is thus fixed inside of each body 34 and the obturator extends to the distal end of the catheter). The cap 33 of each male luer lock freely embraces each body 34 and is screwed on the female luer lock 29.

The female and male luer locks and Y-adapter are molded from a hard commercially available plastic. The Y-adapter is preferably weldable to the material of the tubing D.

The obturators 31 and 32 are elongated lengths of plastic, preferably Teflon (trade mark) or polyurethane. The plastic is flexible and has a higher modulus of elasticity than the material of the tubing D and has a glossy surface.

One obturator 31 extends to the distal end of the venous lumen 18 and has the same cross-sectional shape (shown in FIGS. 2m through 2s) as the lumen 18 and is hollow. The obturator 31 has an opening and a stainless steel guidewire 41 extends through it. The other obturator 32 is unperforated (solid) and extends down to the end of the arterial lumen 16 and has the same cross-sectional shape (shown in FIG. 2g through 2l) as the lumen 16. The distal end of each obturator is shaped and polished to fit the end of the lumen.

As explained above, the proximal end of each obturator is fixed inside the body of a male luer lock 34. The cap of the male luer lock 33 must be screwed tightly onto the female luer lock 29 so that preferably the silicon elastomer tubing 27 is stretched to a certain extent, to create a certain pressure between the ends of the lumen and the obturator and there is a certain prestressed pressure in the obturator itself and thus prestressed tension in the wall of the tubing body A.

After both the obturators and guidewire are assembled within the lumens, there is preferably substantially no empty space in the catheter body A throughout its length and the body A cannot be squashed by pinching or kneading between the thumb and index finger.

At the proximal end, the relative position of the lumen 16 and the obturator 32 and the lumen 18 and the obturator 31 may be exchanged with each other in the Y-adapter, i.e. the lumen 18 and the obturator 31 may be placed in the straight channel of the Y-adapter and the lumen 16 and obturator 32 in the other channel. The obturators should be pulled out as soon as possible after the catheter is inserted in the body. Blood clotting may take place if the obturator is left in place too long.

Among the important features of the construction described are the following:

(a) An obturator extends within each lumen of the catheter A. This effectively prevents the catheter from kinking when inserted into the body of a patient. After insertion, the obturators and guidewire are withdrawn so that the catheter provides for the greatest possible blood flow.

(b) The way in which a smooth bi-branched tubular construction is formed at the proximal end of the tubing body A and is fixed inside the branched adapter, e.g. the Y-adapter, or a Δ-adapter to be described. The branched adapter can have one arcuate deviating channel which makes it possible for an obturator to be readily inserted and pulled out through each lumen. This does away with a dead end in the Y-adapter normally present in other catheters. This eliminates interference with the blood flow.

(c) The way in which a single venous lumen construction is formed at the distal end of the tubing body A. It has the same cross-section as that of the venous lumen in the body of the catheter. This allows the obturator to work efficiently in preventing the body of the catheter from kinking.

(d) The construction lends itself to several different novel cross-sectional shapes for the body of the catheter, namely flat circular or flat sided circular, elliptical, rhombic with arcuate sides and oval. These shapes are shown in FIGS. 2b to 2f. These shapes are preferred to the conventional circular shape shown in FIG. 2a. The aim is to provide the optimal cross-section of a septum walled double lumen tubing. It is desirable that the lumen cross-sectional area be substantially the maximum for the total cross-sectional area of the tubing. Calculations shown that, when the ratio between the long and short axis, alpha of the flat-circle cross-section which consists of two half circles and a rectangle between is 1.5, i.e. the long axis should be 1.5 times the short axis, but the ratio alpha in a circle is 1.0. On the other hand, the best ratio beta of the elliptic cross-section is 1.637 (1+2/pi) but the ratio beta in a circle is 1.0 also. For a rhombic cross-section it would be higher.

Second, in a circular cross-section tubing, the septum wall is longer than the others. But, the shorter it is, the more rigid and, the stronger it is as a lateral support to the wall of the tubing. This means that the body of the tubing in other shapes is stronger than that of the circular one and the wall of the tubing can be thinner, i.e. the lumens may be larger.

Third, the size of the Y-adapter may be smaller and the shape of the distal part of the single lumen part is better than that of the circular tubing because the septum wall is shorter.

All things considered, the ratio between the long and the short axis, 1.5 may be too high for the cross-section, and a lower one of 1.1, 1.2, 1.3 etc. could be selected rather than a circle.

Manufacturing Procedures

Preferred manufacturing procedures, according to the invention are as follows.

Part 1(A) FIGS. 1a to 18—Materials and Equipment

The raw materials and equipment required, which are commercially available, are as follows:

(1) Raw tubing D and 14 for the body of the catheter.

The material of both must be uniform, weldable, glossy smooth, and non-thrombogenic polyurethane or polyethylene. It is preferably transparent. D is a septum walled double lumen tubing and has arterial and venous lumens 16 and 18 respectively. 14 is an extension of the lumen 18 in the tubing D. The cross-sections of tubing D are shown in FIGS. 2a, 2b, 2c, 2d, 2e and 2f, and tubing 14 in FIGS. 3a, 3b, 3c, 3d, 3e and 3f. Tubing 14 may be omitted, as will be explained later.

The cross-sectional dimensions of the tubing D may be as follows (for subclavian veins only). The diameter of the catheter tube having a circular cross-section, as shown in FIG. 2a, is preferably about 10 French (0.131 inches) and could range from 9 to 11 French. For the non-circular tubing shown in FIGS. 2b to 2f, the short axis of the cross-section is about 8 to 10 French (0.104 to 0.131 inches). The long axis of the cross-section is about 10 French to 12 French (0.131 to 0.157 inches). The thickness of the wall in any of these embodiments should preferably be about 0.10 inches and could range from about 0.009 inches to about 0.011 inches. The septum wall may be slightly thicker than the wall of the tubing. It should be understood that for other veins than subclavian, these dimensions may vary.

(2) Plastic rods 31, 32 for the body of the obturators. 32 is solid. 31 is hollow to accommodate a stainless steel guidewire. The material of the rods 31,32 may be polyurethane (weldable to the male luer lock) or Teflon (unweldable) and must be harder than that of the tubing D, 14. The modulus of elasticity (or deformation) is higher, and the surfaces of the rods must be smooth and glossy. These cross-sections are shown in FIGS. 2g, 2h, 2i, 2j, 2k, 2l, 2m, 2n, 2p, 2q, 2r and 2s relative to the tubing D.

(3) Rods 20,22,48,49 for welding.

The material of these rods may be Teflon (flexible) or steel (rigid) or a combination of Teflon and steel. Teflon is better than steel. The rigid part of the rods 48 and 49 may consist of a Teflon sheath and a steel core. The surface of these rods must be very smooth and glossy. Their cross-section is such that they fit tightly in the lumens of the tubing D. The rods 48,49 and 20,22 are slightly larger in cross-sectional area than the rod 32 or at least the same size.

(4) Silicon elastomer sleeve for welding 24,25,26,28,30.

The inside shape and size of the cross-section are the same as the outside shape and size of the tubing D, 14, Y-adapter or the body of the male luer lock, respectively. In case it is not a circle, there should be two or more bright, straight dotted index lines on the inside or outside surface of the sleeve. For example, if the cross-section is an ellipse, there must be at least two dotted index lines to indicate both ends of the short axis in the ellipse throughout the length of the silicon sleeve. The thickness of the wall of the silicon sleeve is about half of the average of the inside diameter.

(5) The Y-adapter B or Δ-adapter and the male-female luer locks 29, 33, 34 and the silicon elastomer tubing 23, 27 which fit the ends of the Y-adapter and the luer locks for assembly.

The material of the Y-adapter and luer locks is inflexible and transparent, e.g. a polycarbonate. And, the material of the Y-adapter is preferably selected so as to be weldable to that of limbs 21 and 19.

(6) Soldering irons E and H with a temperature control device.

Figure 10:
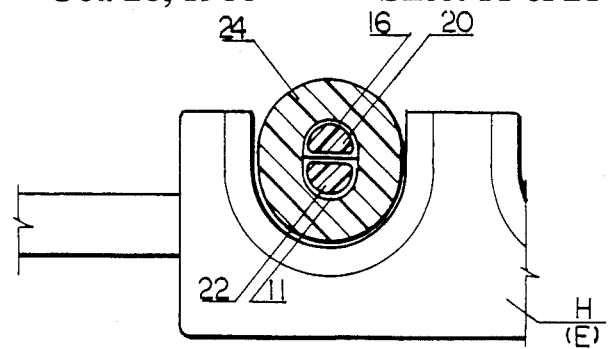

These have iron blocks E and H with four or more channels which fit the outside shapes and sizes of the silicon tubing G (FIG. 10). The thickness of the iron blocks or the width of the working edge of the channel in the block H is typically 3 to 4 mm and in E typically 6 to 7 mm.

(7) Ultrasonic heating apparatus. This may be employed.

(8) Liquid freon.

(9) Alcohol.

Figure 7:
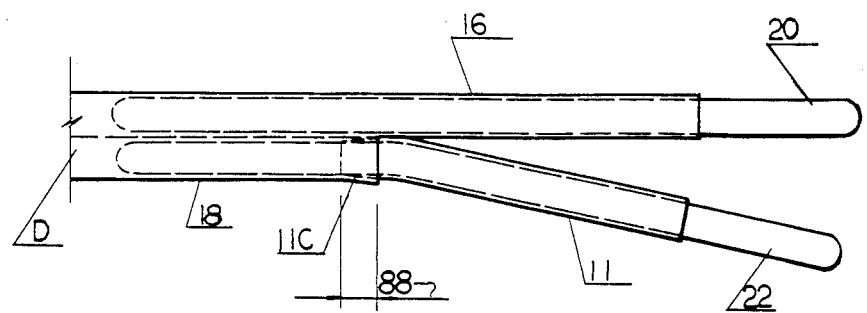
FIGS. 7 to 10 are fragmentary longitudinal cross-sectional views illustrating steps in the fashioning of the proximal end of the tubing.
Figure 8:
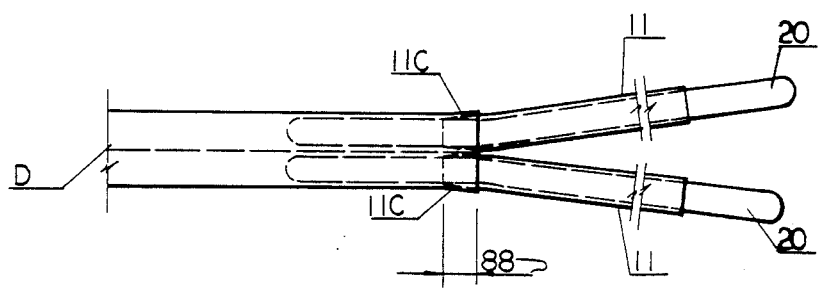
Figure 9:
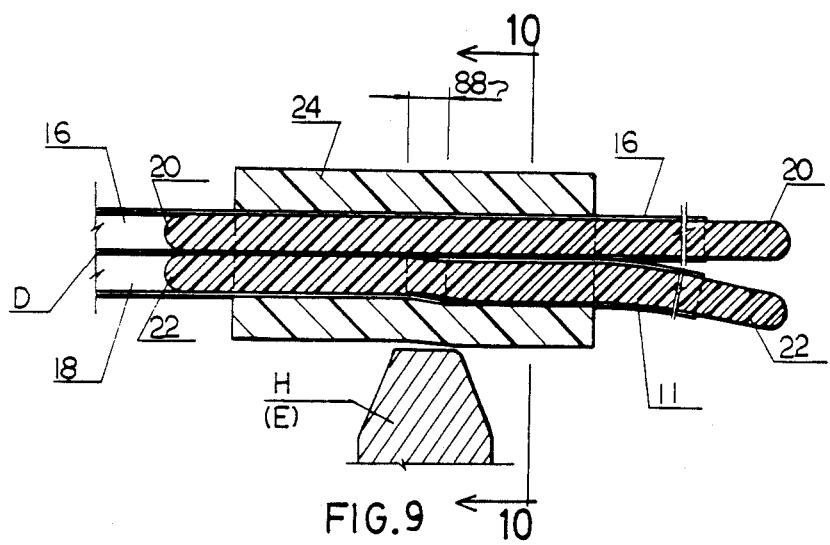

Part 1(B), FIGS. 4a to 4n and FIGS. 7 to 14—Fashioning the Proximal End (1) An assembly is made as shown in FIGS. 7, 8 and 9 proceeding through the following steps:

(i) At the proximal end of the tubing D, part of the lumen 18 is removed, for example, by cutting with a blade, leaving the single lumen 16 alone protruding from the proximal end (see FIG. 7).

(ii) A length of tubing 14 is cut to provide a limb 11, and one end of the limb 11 is sanded to provide an outside taper on its end as at 11c (see FIG. 7). The sanded end is then cleaned with alcohol.

(iii) The ends of rod 20 and 22 are sanded and polished to be round and shiny smooth and are then inserted into the proximal ends of the lumens 16 and 18 respectively (see FIG. 7).

(iv) The lumen 11 is then pushed onto the rod 22 until its tapered end enters the end of the lumen 18. The end of the lumen 18 is stretched and enlarged by the entry of the limb 11. The width of the overlap 88 is 1 to 3 mm (see FIG. 7).

The following should be noted.

In the case of a circular or flat circular, elliptical or arcuate sides rhombus tubing D, the tubing 14 may be omitted and the limb 11 provided by cutting off a length of a single lumen 16 which is left protruding from the proximal end.

Or, the step (i) may be omitted and the tubing 14 cut to provide two limbs 11 which are sanded and then pushed onto the rods 20 and 22 (see FIG. 8).

Because both lumens of the circular, flat circular or elliptical or arcuate sided rhombus tubing D are the same shape, the rods 20 and 22 may be the same.

(v) A length of silicon elastomer tubing 24 is cut off to provide a sleeve 24. The sleeve 24 is first dipped into liquid Freon, which causes its enlargement and lubrication. Then, the sleeve 24 is put on the assembly. See FIGS. 9 and 10. Preferably one hundred or more assemblies are prepared to be ready for the next step.

(2) After the Freon has dried thoroughly, the assembly is placed in a channel on the iron E. For productivity there should be four or more assemblies handled at the same time.

The heating elements E are first activated to preheat the adjoining part of the assembly to a temperature higher than 100° C., but lower than the melting (fusion) point of the tubing material (FIGS. 9 and 10).

(3) Then, one of the assemblies which is preheated sufficiently, usually 30 to 50 seconds, is removed from the preheating iron E to the welding iron H (FIGS. 9 and 10).

For productivity, the number of the assemblies in the iron E should be more than three, i.e. before the next one is taken away, a cold assembly should be placed in the iron where the last one was. In other words, the number of vacant channels in the iron E should not be more than one.

The welding iron H is activated to heat a narrow band of the assembly so that the tube material in the vicinity of the overlap 88 of the limb 11 with the end of the lumen is melted enough so that the material flows smoothly, leaving an imperceptible joint in which the respective parts are to all intents and purposes integral. The heating should not be for long enough to degrade the tubing material.

The temperature of the iron H must be higher than the melting point of the tube material (the higher the better), but must be lower than the burning point, i.e. carbonizing point of the tube material and lower than the melting point of the rods 20 and 22 material.

The following should be noted. The temperature of the welding iron can be conveniently controlled accurately and steadily. Step 2 may be omitted. Steps 2 and 3 can be changed as follows. The temperature of the iron H is properly adjusted to be higher than the melting point of the tube material and the temperature is kept substantially constant. Four or more assemblies are placed in the iron H at the same time (see FIGS. 9 and 10). A narrow band of the assembly is heated by the iron H. So after a couple of minutes the tube material in the vicinity of the overlap of the limb with the end of the lumen is melted so that the material flows smoothly leaving an imperceptible joint in which the respective parts are to all intents and purposes integral.

When one of the assemblies is heated sufficiently as above, it is removed from the heater and a cold assembly placed in the heater. When observation shows that it is heated sufficiently, it is removed and another cold assembly placed in the heater, and so on.

Step 3 may be improved by using ultrasonic apparatus. In that case, the width of the narrow band of the assembly, which is subjected to heating, should be controlled quite accurately and steadily.

Figure 11:
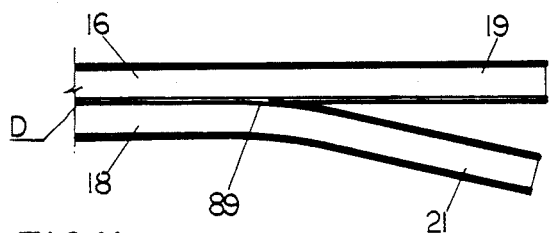
FIG. 11 is a fragmentary longitudinal cross-section through tubing resulting from the procedure of FIGS. 7 to 10.

Steps 2 and 3 may be carried out at a rate of 60 to 100 assemblies or more per hour per operator. (4) The assembly is removed from the heater and air-cooled. Then, the silicon sleeve 24 and the Teflon rods 20, 22 are removed. The branched tubular construction is formed at the proximal end of the tubing D (as shown in FIG. 11). Two limbs 19, 21 deviate at 89 to form two extensions, one for each lumen.

(5) The branched construction is then fixed inside the Y-adapter or Δ-adapter.

A new Y-adapter and 66-type adapter are designed as shown in FIGS. 4a, 4b, 4c, 4i and 4j.

In a Y-adapter there is an arcuate deviating channel 79. After the Y-adapter is molded, the inner mold in this channel can be removed with a circular withdrawal motion. The arcuate channel 79 is better adapted for the obturators than a straight deviating channel. The branches 19, 21 are inserted through the single channel of the Y-adapter into its deviating channels 78, 79. The ends of the branches 19, 21 are then welded inside the ends of the channels 78, 79 at point 81.

Figure 12:
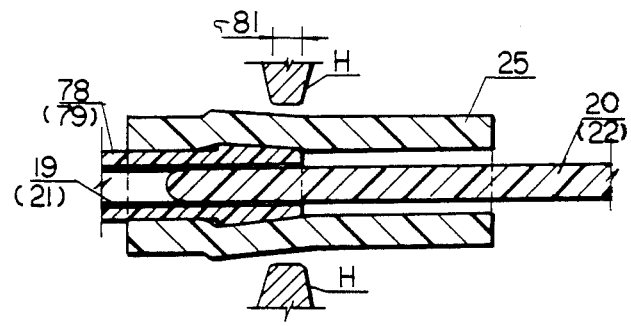
FIGS. 12 and 13 are longitudinal fragmentary cross-sectional views illustrating a way of connecting the tubing to a Y-adapter.

One welding method is shown in FIG. 12. A silicon sleeve 25 is put on each end of the channesl 78, 79 and a rod 20 or 22 inserted into each end of the branches 19, 21. The assembly is then heated in the iron H. After the ends of the channel and branch have been melted and flowed together, the assembly is removed and air-cooled. After it is cooled, the sleeve 25 and the rods 20, 22 are removed. Then, the end which is melted is cut straight and rounded by sanding.

Figure 13:
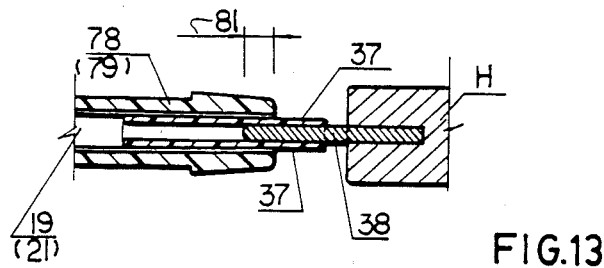

Another method is shown in FIG. 13. A thin-walled Teflon sleeve 37 is inserted with a tight fit into the branch 19 or 21. A steel rod 38 which fits the inside of the sleeve 37 is heated in the iron H and then inserted into the sleeve 37, heating the end of the branch 19 or 21 through the Teflon sleeve 37.

Figure 4F:
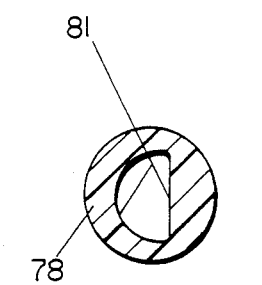
Figure 4E:
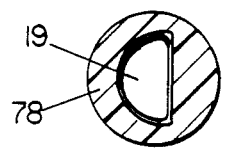
Figure 4D:
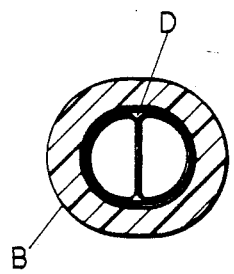
Figure 4A:
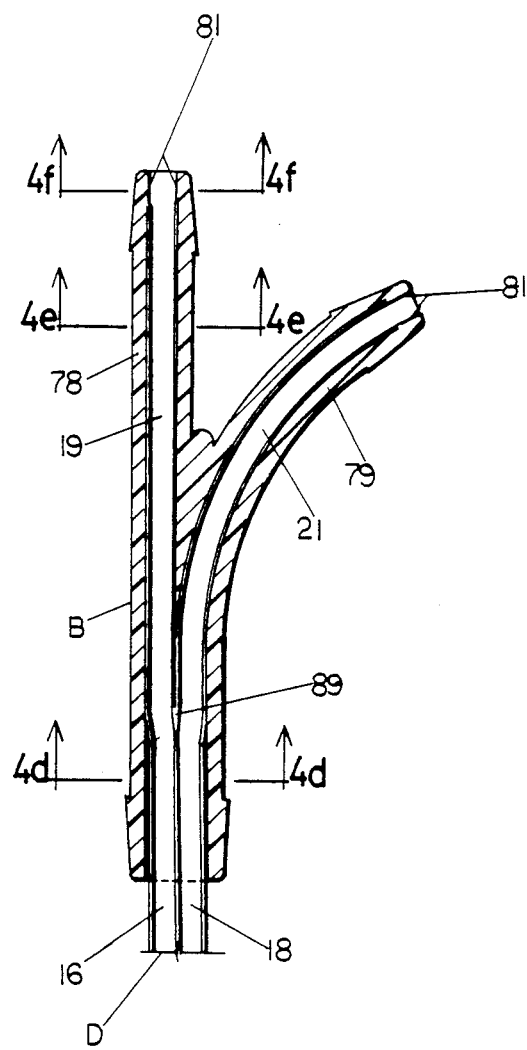
FIG. 4a is a longitudinal cross-section through a proximal end part of a catheter showing the branched body of the catheter within a Y-adapter.

In the meantime, the end of the channel 78 or 79 is also heated. After the end of the branch 19 or 21 and the inside of the channel 78 or 79 are melted so that the material flows together, the Y-adapter with the sleeve 37 is removed and air-cooled. After cooling, the sleeve 37 is removed. No cutting nor sanding is required. For this reason, the method just described is faster than the first method. The result of both is shown in FIG. 4a.

In another method, the deviating channels 78, 79 are short, say 6 to 10 mm in length, leaving the branches 19, 21 protruding, with the ends of branches 19, 21 flared and perforated. Then, a compression molded end, which will be integrated with the end of each branch (19 or 21) is molded and integrated with each end of the channels 78, 79. The resulting product is as shown in FIG. 4a.

Figure 4C:
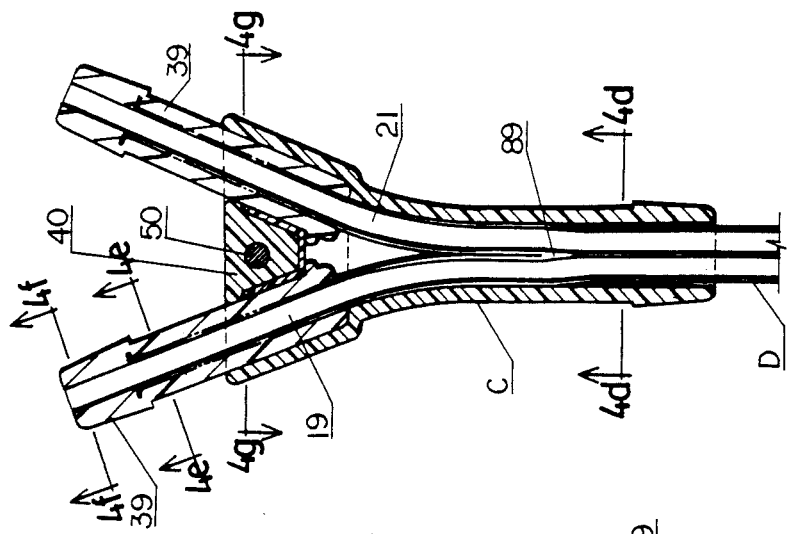
FIG. 4c is a further alternate form of proximal end of a catheter, according to the invention.
Figure 4H:
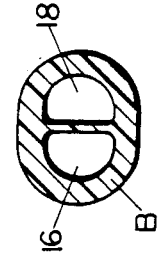
Figure 4G:
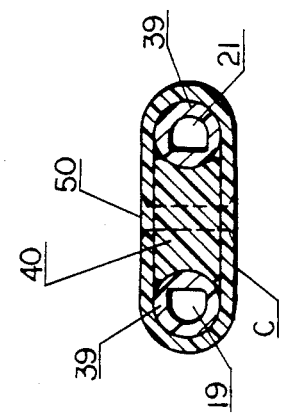

A modified type of branched adapter C is shown in FIG. 4c. A connector 39 is molded on the end of each branch 78, 79). Then, the catheter is inserted through the modified Y-adapter C and the connectors 39 are held in place by a plastic block 40 and a screw 50.

Another way of making the proximal end part is as follows. See FIG. 14.

The adapter C is molded at the proximal end of the tubing D. At the same time, the end of tubing D is welded integrally to the adapter forming a branched tubular construction inside the adapter.

The prerequisites are the following. The material of the adapter is weldable to the tubing D and is inflexible, and as hard as possible.

Figure 14:
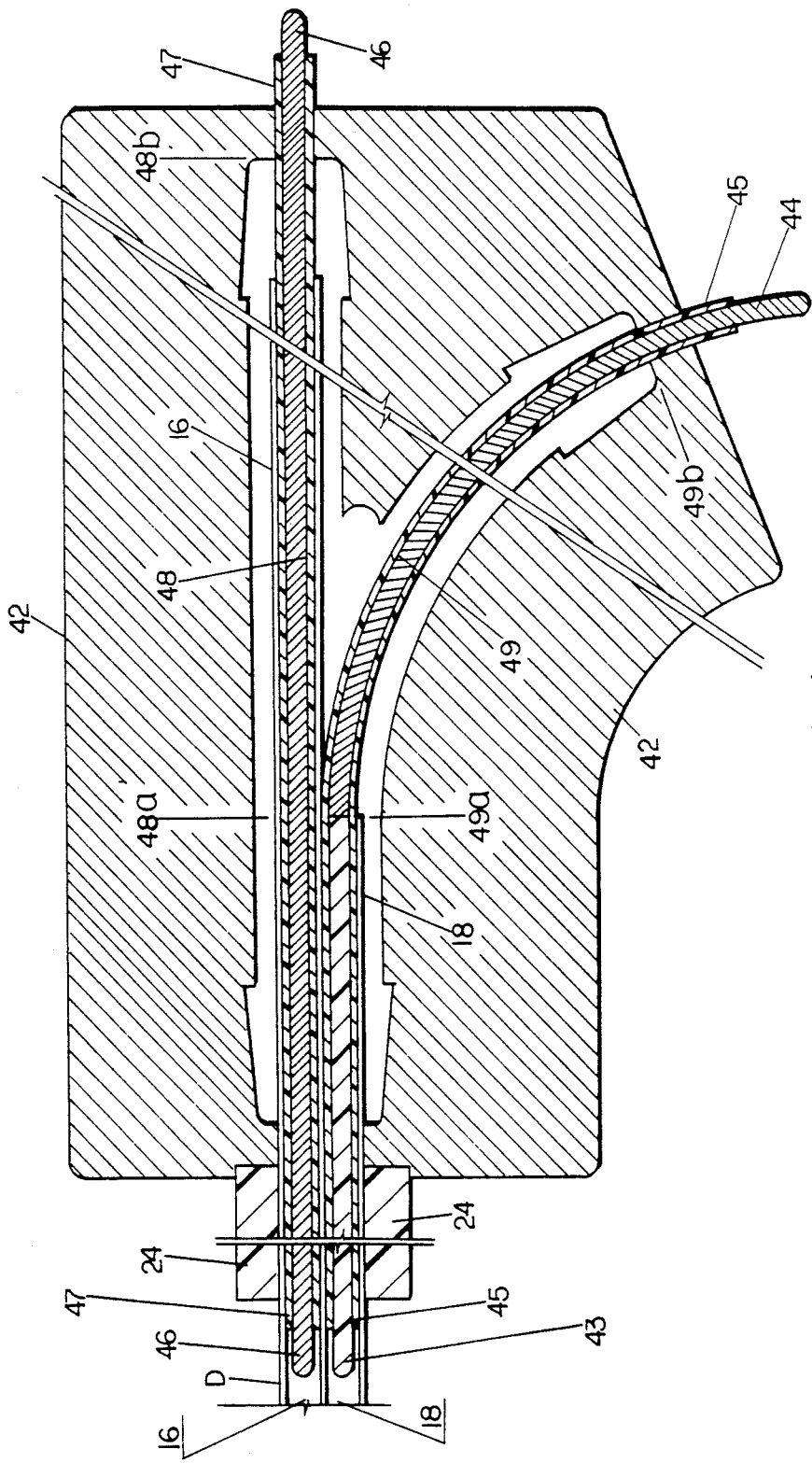
FIG. 14 is a fragmentary longitudinal cross-section showing another way of fashioning the proximal end of tubing at the same time as forming a Y-adapter.

A straight rod 48 is selected of the same cross-section as the rod 20, i.e. it fits tightly into the arterial lumen 16. The rod 48 must be rigid and inflexible. It may be made of pure steel or of a Teflon sheath 47 with a steel rod 46 as a rigid core. This is in effect a steel rod 46 with a Teflon sheath 47 which may be quite thin, as shown in FIG. 14.

An arcuate rod 49 is selected to have the same cross-section as the rod 22, i.e. it fits tightly in the venous lumen 18. The straight part of the rod 49 should be flexible, but its arcuate part should be relatively rigid, for example, Teflon sheath 45 with a steel core 44. The straight part has a flexible Teflon core 43.

The rods 48 and 49 form the inner molds. Their size may be progressively larger from the point 48a, 49a to the end 48b, 49b, as shown in FIG. 14.

A mold 42 is selected to form the outside shape and size of the Y-adapter.

At the proximal end of the tubing D, part of the lumen 18 is removed, leaving the lumen 16 protruding.

The rods 48, 49 are inserted into the corresponding lumens respectively.

The assembly is placed in the mold 42, leaving the rods 48, 49 protruding. A length of silicon sleeve 24 is put on the outside of the tubing D as shown in FIG. 14.

According to one method, the melted plastic to form the Y-adapter is injected into the mold 42. The mold 42 is then heated until the tubing is melted sufficiently to weld the Y-adapter to the tubing, specially in the vicinity of the points 48a and 49a.

Figure 4B:
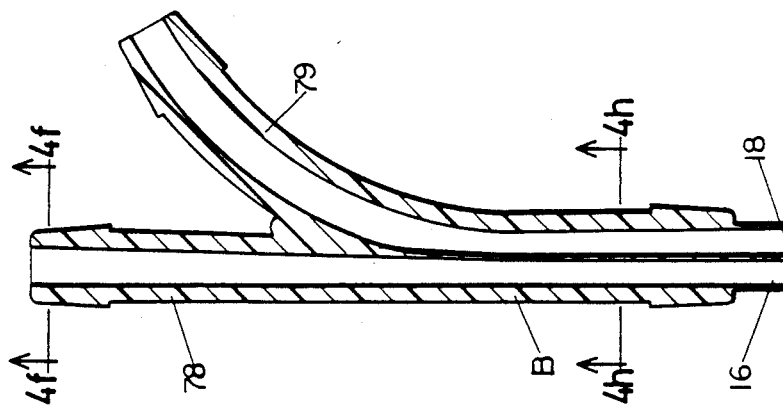

The mold 42 is then cooled. After it is cooled, the mold 42 and the rods 48, 49 are removed. The resulting product is shown in FIG. 4b.

According to another method, the end of the lumen 16 is flared, the lumen 16 is perforated near the end and then the Y-adapter is molded on the proximal end of the tubing and cooled, the outside mold 42 of the Y-adapter is removed, but the rods 48, 49 remain in the inner mold. Then, melting is effected in the vicinity of the point 49a, by a welding iron H and a length of silicon sleeve is put onto the Y-adapter. After the Y-adapter is melted and cooled, the rods 48, 49 and the silicon sleeve are finally removed. The resulting product is shown in FIG. 4i.

According to a still further method, the end of both lumens are first flared and both lumens perforated near their ends. Then, the Y-adapted is molded. The resulting product is shown in FIG. 4j.

Part 1(C) FIGS. 15 to 18—Fashioning the Distal End

The distal end of the catheter A is manufactured as follows.

Figure 15:
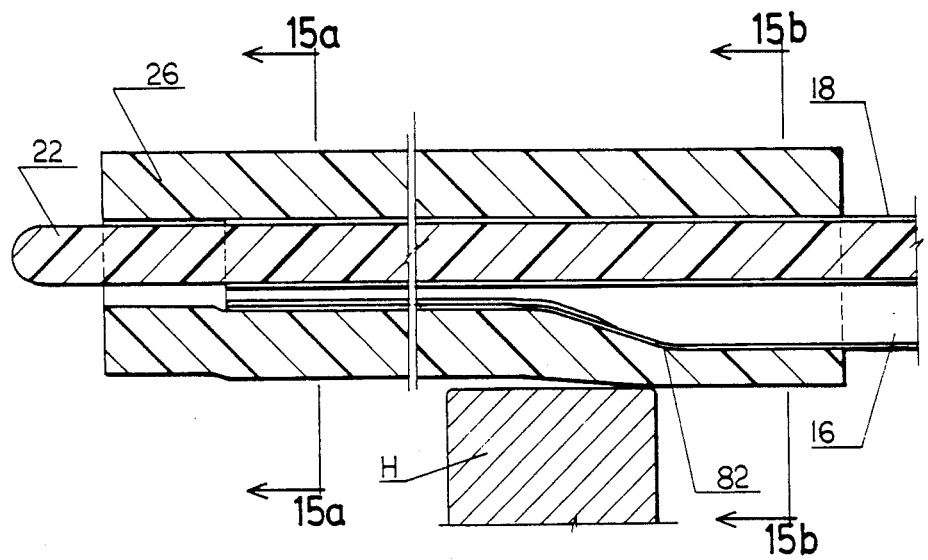
Figure 15A:
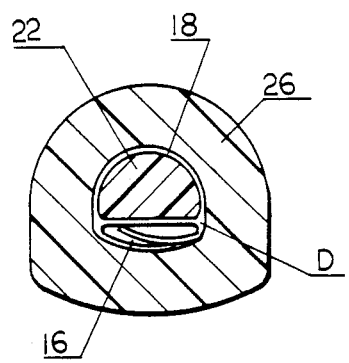
Figure 15B:
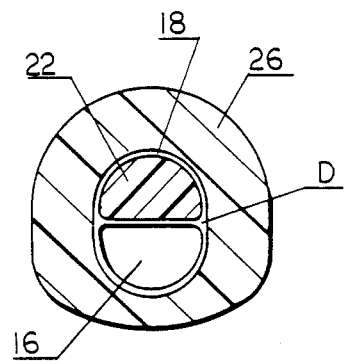

(1) An assembly is made up, as shown in FIG. 15, by the following steps:

(i) The lumen 16 is slit lengthwise to a predetermined length at the distal end part of the tubing A;

(ii) A length of Teflon rod 22, sanded and polished on its ends, is inserted into the lumen 18 and protrudes beyond it;

(iii) A length of silicon tubing F is cut off to provide a sleeve 26 (about 50 mm in length). The sleeve 26 is first dipped into liquid Freon which causes it to enlarge and also lubricates it. Then, the sleeve 26 is put on the assembly (see FIG. 15).

Preferably, a large number, say, one hundred or more, assemblies are made up at the same time for the next step.

(2) After the Freon has dried thoroughly, the welding iron H is activated to heat the side of the assembly on which the lumen 16 is slitted and the assembly is moved relative to the iron to make sure the heated zone is moved from a point 82 to the tip of the tubing A. The welding temperature should be high enough and the speed of the assembly slow enough to cause fusion of the overlapping part of the slit portion of the lumen 16. The elasticity of the silicon sleeve 26 will cause the molten material to flow against the wall of the lumen 18 and will become integral with it when it solidifies.

Figure 1A:
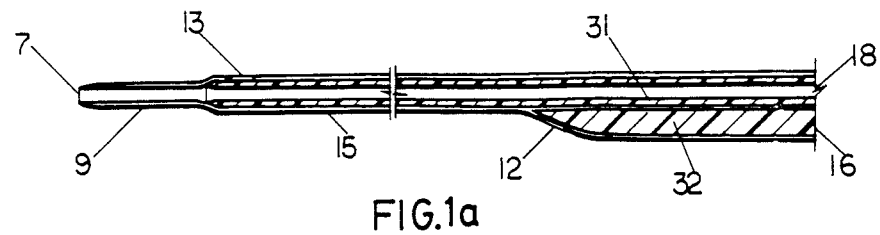
FIGS. 1a to 1e are enlarged longitudinal fragmentary cross-sectional views of the distal end parts of several different catheters of the general structure illustrated in FIG. 1.

(3) After it is melted sufficiently, the assembly is removed from the iron and air-cooled. When it has cooled sufficiently, the silicon sleeve 26 and the Teflon rod 22 are removed. The result is shown in FIG. 1a or 1c.

Part 1(D)—Making the Distal End (Alternative)

An alternative way of making the distal end is as follows.

Figure 16:
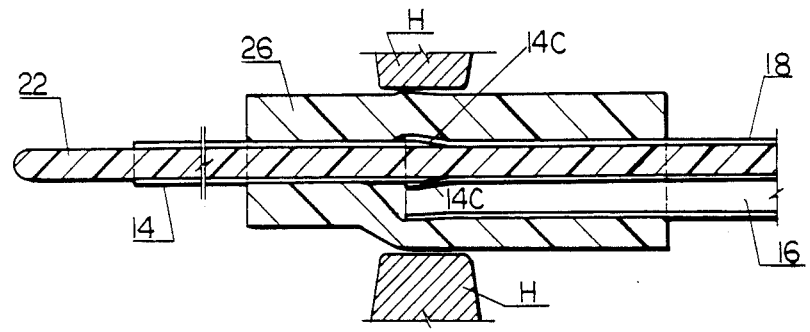

(1) An assembly is made up, as shown in FIG. 16 by the following steps:

(i) A length of raw plastic tubing is cut to provide an extension 14. The extension 14 is sanded to provide an outside taper on its end as at 14c, like limb 11 (FIG. 7). The sanded end is then cleaned with alcohol.

(ii) The rod 22, sanded and polished on its ends, is inserted into the lumen 18 and protrudes beyond it.

(iii) The extension 14 is then pushed into the rod 22 until its tapered end enters the end of the lumen 18. The end of the lumen 18 is stretched and enlarged by the entry of the extension 14. The width of the overlap is preferably 1 to 3 mm.

(iv) A length of silicon elastomer tubing 26 is cut off to provide a sleeve 26 (about 20 mm in length). The sleeve 26 is first dipped in liquid Freon which causes it to enlarge and lubricates it. Then, the sleeve 26 is put on the assembly (see FIG. 16).

Preferably, a number of assemblies, say one hundred or more, are made up at the same time for the next step.

(2) After the Freon has dried thoroughly, the assembly is placed in a channel on the iron E. For productivity, there should be four or more assemblies placed in the channel at the same time.

The heating elements E are first activited to preheat the adjoining part of the assembly to a temperature higher than 100° C., but lower than the melting (fusion) point of the tubing material.

(3) Then, one of the assemblies, which is preheated sufficiently, is taken away from the preheating iron E to be placed on the welding iron H.

The welding iron H is activated to heat a band, which may be wider than that at the proximal end of the assembly, so that, the tube material in the vicinity of the overlap of the extension 14 with the end of the tubing D is melted sufficiently so that the material flows smoothly and the elasticity of the silicon sleeve 26 will cause the molten material of the wall at the end of the lumen 16 to flow against the wall of the lumen 18, leaving an imperceptible joint. The end of the extension 14 and the lumen 18, the wall at the end of the lumen 16, are to all intents and purposes, integral, as shown in FIG. 1a or 1c.

The speed of the steps (2), (3) should preferably be, for example, 60 to 100 assemblies per hour per operator.

Figures 17A, 17C, 17D:
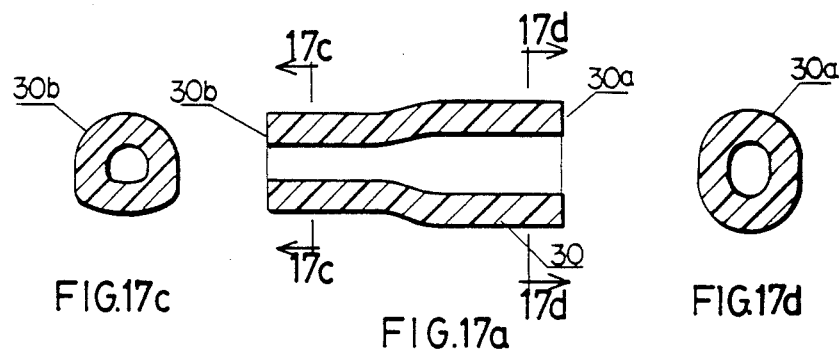

Using a special silicon elastomer sleeve 30, having the longitudinal section as shown in FIG. 17a, and the cross-section at an end 30a, the same as silicon tubing 24, and this cross-section (FIG. 17d), the other end 30b is the same as that of the silicon tubing 26 (FIG. 17), and which is commercially available, the assembly could be changed as follows.

The extension 14 is the same as described above.

Figure 17B:
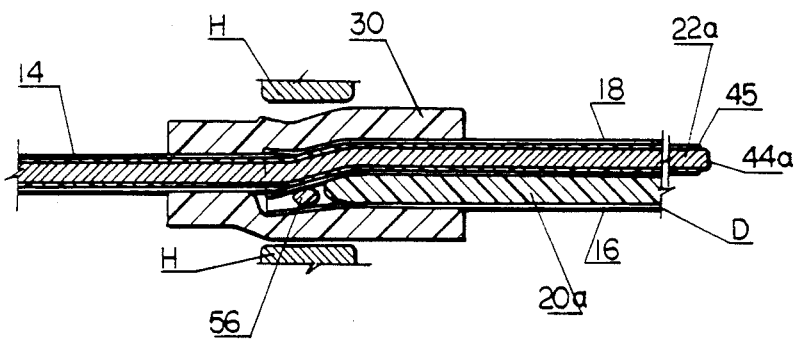

A rod 20a, rounded at the end by sanding and polishing, is inserted in the lumen 16 to the extent shown in FIG. 17b.

A rod 22a consists of a Teflon sheath 45 and a steel core 44a which is curved at the predetermined points as shown in FIG. 17b. The rod 22a, which is rigid and curved, is inserted in the lumen 18, as shown in FIG. 17b. A pellet 56, of the same plastic material as that of the tubing D, is placed in the lumen 16 just ahead of the rod 20a.

Then, the sleeve 30 is dipped in liquid Freon and put on the assembly, as shown in FIG. 17b.

There should be a dotted bright line in the wall of the silicon sleeve 30, as a visual index to show the changing cross-section, i.e. so as to indicate the relative positions of the rods 22a, 20a, and tubing 14, D and sleeve 30.

After the Freon has dried thoroughly, the assembly is preheated and welded as above. The width of the molten zone is wider than in the form of the invention shown in FIG. 9 so that the iron block H must be wider.

Figure 1B:
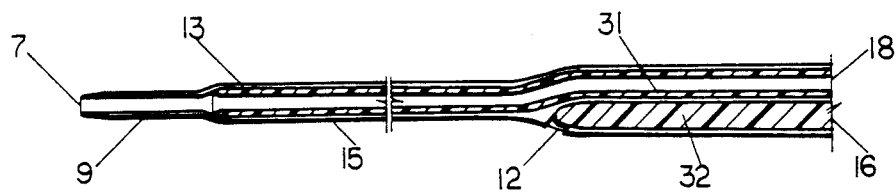
Figure 1C:
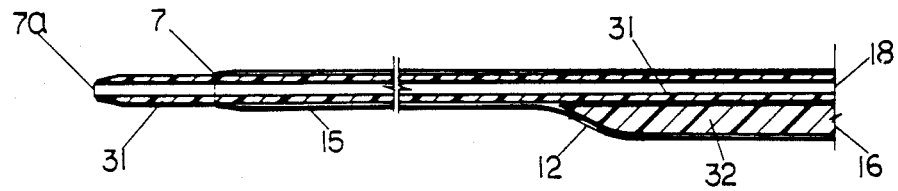

The result is shown in FIG. 1b. It is superior to that in FIG. 1a, because there is no sharp corner at the end of the lumen 16.

Another way of fashioning the distal end part is as follows.

(1) A length of rod 61 is selected of polyurethane or polyethylene which is flexible and harder than the material of tubing D and is readily weldable to it. The cross-section of the rod 61 is the same as that of the arterial lumen 16 of the tubing D, i.e. the rod 61 tightly fits the lumen 16.

(2) The distal end of the tubing D is tapered as shown in FIG. 18.

(3) An assembly is made up of the following steps, shown in FIG. 18:

(i) An end 61a of the rod 61 is sanded and polished to fit the end of the arterial lumen 16. The other end of the rod 61 is cut as shown in FIGS. 18 and 1e and 1f.

(ii) A length of Teflon rod 20 is cut to fit the cut end of the rod 61.

(iii) The rods 61 and 20 are inserted into the arterial lumen 16. A length of Teflon 22 is inserted into the venous lumen 18. The silicon sleeve 24 is then put on.

(4) The assembly is then placed in the iron H. The end part 68 of the rod 61 is heated. After the end part 68 of the rod 61 is melted and welded with the wall of tubing D, the assembly is removed and air-cooled. Then, the rods, 20, 22 and silicon sleeve 34 are removed.

Figure 1D:
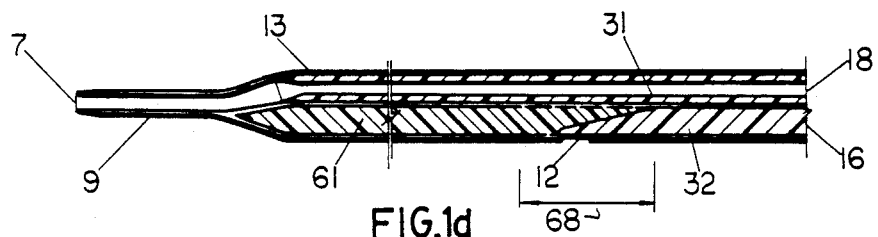
Figure 1E:
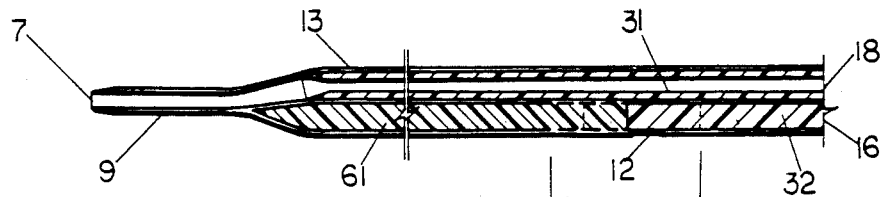
Figure 1F:
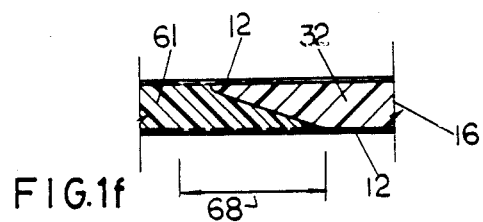
FIG. 1f is a fragmentary transverse cross-section on the scale of FIGS. 1a to 1e of the part of the catheter shown in FIG. 1e at right angles to the view of those Figs.

The result is shown in FIGS. 1d and 1e (after the tip is sanded).

Part 1(E) FIGS. 5 and 6a to 6h—Making the Obturators

The obturators must fulfil the quality requirements described. The body of the obturator is custom ordered.

The distal end of the solid obturator 32 is merely sanded and polished to fit the end of the lumen 16.

The distal end of the hollow obturator 31 should be flared first to enlarge the end hole in order to receive the guidewire. Then, the outside of the end is sanded and polished to fit the end of the lumen 18.

The proximal end of the obturator may be welded inside of the body of the male luer lock 34 as shown in FIG. 5. H is a melting iron, 28 a length of silicon elastomer sleeve, 10 a steel rod within the hollow obturator 31. The resulting product is shown in FIGS. 6c and 6d.

When the obturators are made from Teflon and not weldable to the body 34, the proximal end of the obturators must be indented (for the solid obturator 32) or perforated (for the hollow one 31) or flared at the tip. Then, the body 34 of the male luer lock is molded on the end, as shown in FIGS. 6a and 6b. If the body 34 of the male luer lock is custom ordered, then a part of the body 34 is melted on the indented or perforated or flared end of the obturators, as shown in FIG. 5. The result is similar to what is shown in FIGS. 6a and 6b.

The body of the male luer lock 34 must be partially closed at the end tip leaving a small hole for receiving the guidewire, bordered by an annular flange, which is to prevent the hollow obturator 31 coming out at this end. This end should not be melted, so as to avoid the extra step of finishing it.

The length of the obturator must be predetermined.

If the material of the obturator is too hard to make it flexible, some longitudinal straight discontinuous slits may be cut along the length of the body of the obturator to reduce the bend-resisting rigidity but, at the same time, to retain rigidity against lateral pressure.

Alternative Forms of Tubing FIGS. 19 to 28

Another way to overcome the problem of kinking is by manufacturing a special tubing, which inherently prevents kinking. Up to now, the raw tubing for manufacturing various catheters is made from uniform isotropic plastic. Because a double lumen catheter is much larger than a single one and the kinking, i.e. local buckling, occurs much more easily, a non-uniform material is better than a uniform material.

In the field of plastic engineering, varieties of non-uniform, non-isotropic or cominative plastic products can be tailored to improve their mechanical behavior under different loading and working conditions.

The invention contemplates special tubing described below for making the catheter.

One is a "multi-ring link" tubing. It is made from two types of plastic. One plastic is very hard and almost inflexible, i.e. its modulus of elasticity (of deformation) is substantially as high as possible. Another is a soft stretchy elastomer, i.e. its modulus of elasticity is quite low. The tensional strength of both are almost equal. A prerequisite is that they are readily weldable to each other.

Two kinds of rings, inflexible rings and elastic rings made from these two types of plastic are welded together one after another to form tubing. The inflexible hard rings resist squashing (lateral stress). The elastic soft rings make the tubing easily bent. And, the septum wall prevents the tubing from changing in length, i.e. stretching or compressing so the tubing may be bent without kinking.

Another is a "metal spring" plastic tubing and is a combination of a metal spring and soft elastic plastic. The metal spring resists squashing (lateral stress). The plastic wall is easily bent. And, the septum wall keeps the tubing constant in length. The tubing may be bent without kinking.

Figure 24A:
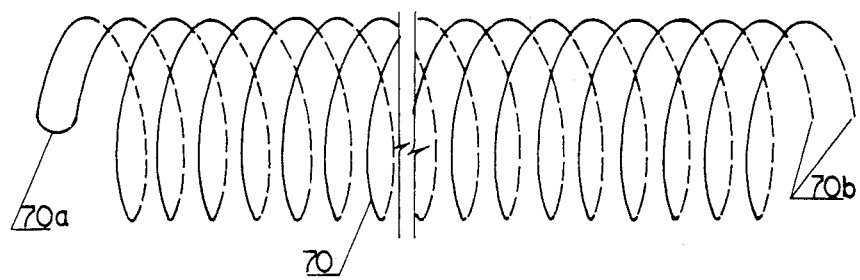
FIG. 24a is a side elevation of a spring used for manufacturing metal spring-plastic tubing.

The distal end of the spring is looped, i.e. doubled back as shown in FIGS. 24a, b, c, so that it will not present a sharp end which might injure the vein of the patient. The length of the spring is such that the two opened free ends of the wire are located inside the Y-adapter and thus away from the body of the patient.

A double lumen catheter formed from either of these two types of tubing does not require obturators.

Alternate Embodiment

FIG. 19 is a side elevation of another form of catheter, according to the invention.

The catheter is made up of a special septum walled double lumen body M having an arterial lumen 16 and a venous lumen 18. The cross-section of the body M may be circular.

The body M extends from the distal end part 55 through an intermediate part 57 to a proximal end part. At the distal end part 55 (the longitudinal section is shown in FIG. 19a), the lumen 16 is plugged by welding at point 62. Then, there is a tapered tip 9, an end hole 7 and two groups of side holes 12, 13 as inlet and outlet of the blood flow. At the proximal end part, there is a flexible tube 23 of silicon elastomer, an inflexible Y-adapter B and a flexible tube 27 of silicon elastomer which connects the end of each branch of the Y-adapter to a female luer lock 29.

This particular construction has the following features:

(a) the body M of the catheter is made up of a special septum walled double lumen tubing which is made up of a combination of two or three different materials so that it is inherently capable of preventing kinking;

(b) the way in which the tubing is manufactured;

(c) the way in which a smooth branched tubular construction is formed at the proximal end of the body M in the same way as described in Procedure Part I, or, at the same time of manufacturing the tubing; and (d) the way in which the lumen 16 is plugged at the distal end part.

The way in which these alternative embodiments of tubing are manufactured will be described in the Manufacturing Procedure Part II.

Manufacturing Procedure Part II FIGS. 19 to 28

(A) The raw materials and equipment, which are commercially available are the following.

(1) A plastic which is hard, almost inflexible, e.g. with very high modulus of elasticity. A plastic which is soft elastic, e.g. with quite low modulus of elasticity. The materials are readily weldable to each other.

(2) The septum walls 74, 75, 76 and 77 are molded as shown in FIG. 20. In the wall 74, the area 74a is hard plastic, the area 74b, 75, 76, 77 are of soft plastic and both 74 and 74b are molded (welded) integrally. The thickness of the wall 76 is half of 74, 75 and 77.

(3) The hard rings 63 made from hard plastic and soft rings 65 made from soft plastic are molded as shown in FIGS. 21 and 21a. The thickness of the ring should be the same as that of the septum walls 74, 75, 77. The width of the ring 63 is wider than twice that of 65.

(4) Tubing 69 and 67, molded from the soft plastic, is shown in FIG. 22.

Figure 24B:
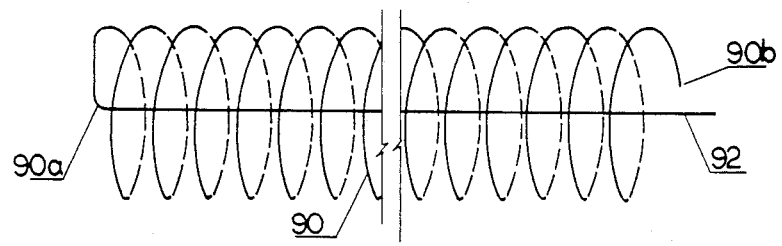
FIG. 24b is a side elevation of another form of spring.
Figure 24C:
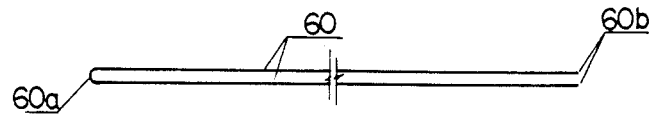
FIG. 24c shows a reinforcing wire for making the septum wall as shown in FIG. 20b, used in another form of plastic tubing.

(5) The metal spring 70 or 90 for the walls of the tubing and the straight wire 60 for the septum wall 75, as shown in FIGS. 24a, 24b and 24c, are made from stainless steel or copper. The distal ends 70a, 90a, 60a are looped back, i.e. are continuous and smoothly curved. The proximal ends 70b, 90b, 60b are free. A straight part 92 and the spring 90 is at the center of the cross-section (see FIG. 25c). The diameter of their wires is half the thickness of the tubing wall, or slightly more.

(6) A silicon elastomer sleeve 94, as shown in FIG. 23.

(7) Two rigid straight rods 84, 85 or 86. 84 is made of steel or of a Teflon sheath with a steel core. The cross-section of the rods are shown in FIGS. 23a and 25b, c, d.

Figure 26:
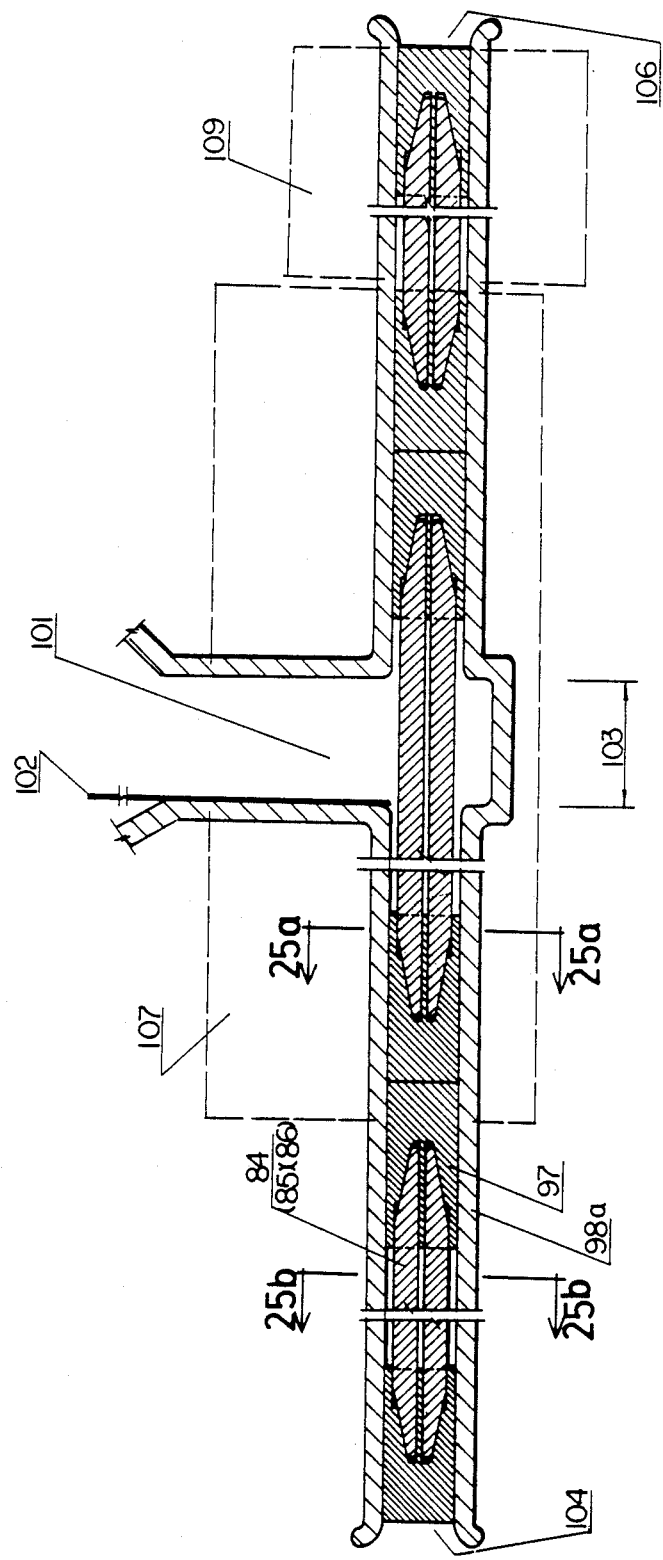
FIG. 26 is a longitudinal cross-section illustrating another assembly in manufacturing metal-spring plastic tubing.

(8) A steel outer mold 98 or 98a, as shown in FIG. 25 or 26.

(9) Heat treating equipment with temperature control device, e.g. an oven. It should be noted that if the pitch in the spring is less than the diameter of the side holes, the special wire of the spring must be curved for each side hole and when the spring is put on the retaining rods, the location of two groups of side holes must be carefully noted.

(B) Manufacturing the multi-ring link tubing is as follows. See FIGS. 20 to 23 and 27, 27a, 27b.

(1) An assembly is made up, as shown in FIG. 23. A septum wall 74 (or 75) is clipped (inserted) between two rods 84 (or 85). See FIG. 23b or 25d. The rings 63 and 65 are put on one after another. The half circle tubing 67 is put on the proximal end. At the proximal end part there is a piece of aluminum foil 93 inserted between the tubing 67. Then, the silicon sleeve 94 is dipped into liquid Freon and put on the assembly.

(2) After the Freon has dried thoroughly, the assemblies are placed in a preheating oven to be heated above 100° C., but below the melting point of the hard and soft plastics, i.e. not melted.

(3) The preheated assembly is then placed in the melting oven to melt the rings 63, 65, the septum wall 74 (or 75) and the tubing 67.

Figure 27:
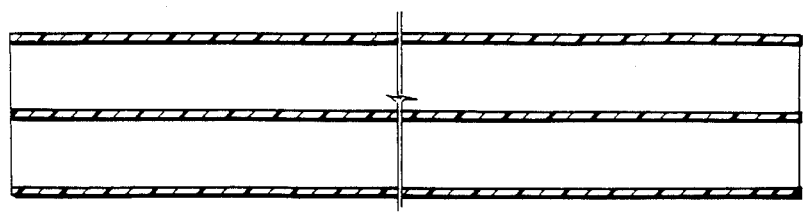
FIG. 27 is a longitudinal cross-section through multi-ring tubing made by the method illustrated in FIG. 23.
Figure 27A:
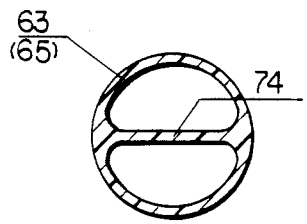
FIG. 27a is a transverse cross-section through the tubing of FIG. 27.
Figure 27B:
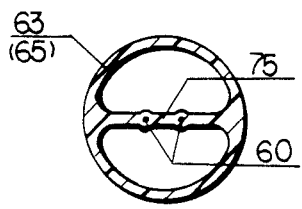
FIG. 27b is a transverse cross-section through slightly modified forms of tubing from that of FIG. 27.

(4) The assembly is finally taken out and cooled. Then the sleeves 94 and the rods 84 (or 86) are removed. The resulting product is shown in FIG. 27.

(5) Fashioning the proximal end as described in Part I, the foil 93 is inserted in the assembly, the steps (1), (2), (3), (4) in Part IB may be omitted.

(6) Fashioning the distal end part, the lumen 16 is plugged as described in Part ID. The rod 61 may be shorter, as shown in FIG. 19a.

(C) Manufacturing the metal spring plastic tubing is as follows. See FIGS. 20a, 20b, 20c, 24a to 26 and 28.

(1) A mold is formed as shown in FIG. 25a. 98 is an outer mold of which the inner surface may be a Teflon tubing, but the body of the mold must be steel. 97 is a steel fixer to fix each end of the rods 84, 85 or 86. The rods 84 or 85 or 86 must match the septum wall 74 or 76 with 92 or 75, respectively (see FIGS. 25b, 25c, 25d). Pieces of film 87 which are very thin and made from soft plastic are inserted between the rods and the spring 70 (or 90).

(2) Molten plastic is injected into the mold 98 through the inlet 51 and the air is expelled by the outlet 53. The whole mold is placed in an oven to keep it slightly hotter than the melting point of the plastic.

(3) After the plastic fills the inside of the mold 98, the mold is removed from the oven and cooled.

Figure 28:
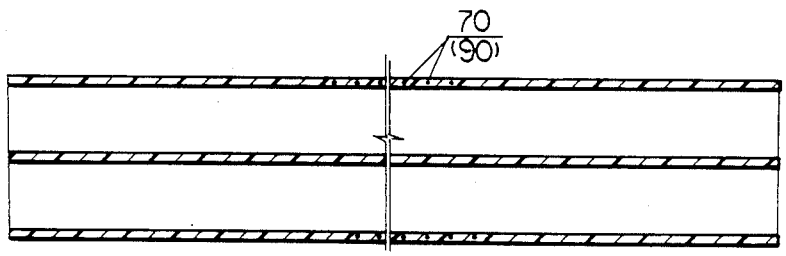
FIG. 28 is a longitudinal cross-section through double lumen tubing having a metal spring embedded in its wall.
Figure 28A:
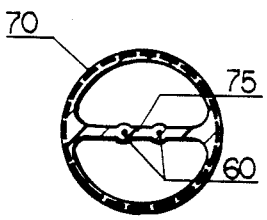
FIG. 28a is a transverse cross-section through tubing having the general form of that of FIG. 28.
Figure 28B:
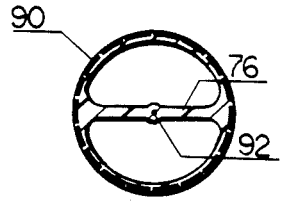

(4) After the mold has cooled sufficiently, the outer mold 98, the fixer 97 and the rods 84 (or 85, 86) are removed. The tubing is then obtained. Steps (5) and (6) are the same as that in B above. The resulting product is shown in FIG. 28.

(D) A continuous manufacturing procedure is shown in FIG. 26.

The outer mold 98a is much longer than 98 (in FIG. 25) and with an open entrance 104 and an open exit 106.

The inner mold is the same as that in FIG. 25 and consists of rod (or 85, 86), spring 70 (or 90), septum walls 74, 75 or 76 and fixers 97.

The container 101 is filled with molten plastic. A small pipe 102 is an outlet for air. 107 is a heating area, where the temperature is kept higher than the melting point of the plastic. 109 is a cooling area where the temperature is dropped from the melting point of the of the plastic down to the normal temperature for example 20° C. at the exit 106.

The inner molds 97, 84 go one by one into the outer mold 98a through the entrance 104 and leave the exit 106 with the metal spring plastic tubing. See FIG. 28. The inner mold is taken apart to obtain the tubing and assembled to be reinserted into the outer mold 98 through the entrance 104.

Advantages

Among the advantages of catheters, according to the invention, are the following:

1. Effectiveness. During insertion of the catheter into the body of a patient, there is no kinking.

2. Size. The body of the catheter is 20 to 30% smaller in cross-sectional area than existing catheters.

3. Blood flow patency. The catheter, despite its smaller size, increases the blood flow potential by 10 to 20% or more over existing products.

4. Blood flow quality. There is no dead space in the branched adapter into which the blood flow can be diverted.

5. Drug retention. When the catheter is left in the body of a patient it effectively retains the drug Heparin. This hinders blood clotting as well as does a single lumen catheter.

6. Manufacture. The catheters of the invention can be made at least as economically as existing products because of their machinability.

7. The body of the catheter with the obturators could be more flexible and pliable than the existing product and could be stiffer, if desired.

I claim:

1. A double lumen catheter for gaining vascular access to the circulatory system of a living being, comprising, an elongated integral plastic thin walled tubular body requiring support against buckling and kinking and having a proximal end part, a distal end part and an intermediate part, the intermediate part having an outer wall and a septum wall providing juxtaposed arterial and venous lumens, the proximal end part being a continuation of the intermediate part and diverging into, integrally connected branches each containing the continuation of a lumen for connection to access tubing leading to a hemodialysis apparatus, the distal end part comprising a continuation of the outer wall tapering to a slender tip merging gradually and smoothly from said body and having an internal guidewire passage leading from the venous lumen and closure means terminating the arterial lumen, short of the tip, including a part of the outer wall tapering inwards to merge with the septum wall, the outside surface of the outer wall being smooth and continuous to offer minimum frictional resistance to insertion into the body of a patient, the inside walls of both lumens being smooth and continuous and the transition of the lumens between the said respective parts being smooth and uninterrupted to facilitate the insertion and removal of obturators into and from the respective lumens to extend from their proximal ends to their distal ends, and the outer wall being provided with at least one blood access orifice in the distal end part of the arterial lumen and at least one blood access orifice in the distal end part of the venous lumen.

2. A double lumen catheter for gaining vascular access to the circulatory system of a patient, as defined in claim 1, having an elongated integral plastic tubular body which has an outer wall and a septum wall providing two juxtaposed lumens in which the cross-section of the outer wall is non-circular and the cross-section has a long axis and a short axis, the septum wall being parallel to the short axis.

3. A catheter, as defined in claim 2, in which said intermediate part is symmetrical and each lumen is of the same cross-sectional shape, and the septum wall is on the short axis of the cross-section.

4. A catheter, as defined in claim 2, in which the intermediate part of the tubing body is non-symmetrical and each lumen has the same area but a different cross-sectional shape.

5. A catheter, as defined in claim 1, in which a branched adapter is connected to and contains the proximal end of the body and part of the branches.

6. A catheter, as defined in claim 1, in which the end of each branch is provided with a connector in the form of a hard plastic tube, a triangular tubular adapter surrounds the proximal end of the body and part of the connector of each branch, and a spacing block is located between respective connectors thereby to establish a fixed spacing between them, said block being fastened to said triangular adapter.

7. A double lumen catheter, as defined in claim 1, in which the thickness of the wall is within the range from 0.009 inches to 0.011 inches.

8. A double lumen catheter, as defined in claim 1, in which the catheter tube is circular and has a cross-sectional diameter within the range from 9 to 11 French.

9. A double lumen catheter, as defined in claim 1, in which the cross-section of the tube is ovoid and the diameter across the narrow axis of the cross-section is from 8 to 10 French and across the long axis is from 10 to 12 French.

10. A double lumen catheter, as defined in claim 1, in which the catheter tube is circular and has a cross-sectional diameter within the range from 9 to 11 French and the catheter wall has a thickness within the range from 0.009 inches to 0.011 inches.

11. A double lumen catheter, as defined in claim 1, in which the cross-section of the tube is ovoid and the width across the narrow axis of the cross-section is from 8 to 10 French and across the long axis is from 10 to 12 French and the outer wall has a thickness within the range from 0.009 to 0.011 inches.

12. A double lumen catheter, as defined in claim 1, in which the tip is integral with the body.

13. A double lumen catheter for gaining vascular access to the circulatory system of a living being, comprising, an elongated integral plastic thin walled tubular body requiring support against buckling and kinking and having a proximal end part, a distal end part and an intermediate part, the intermediate part having an outer wall and a septum wall providing juxtaposed arterial and venous lumens, the proximal end part being a continuation of the intermediate part and the end of each lumen therein being adapted for connection to access tubing leading to a hemodialysis apparatus, the distal end part comprising a continuation of the outer wall tapering to a slender tip merging gradually and smoothly from said body and having an internal guidewire passage leading from the venous lumen and closure means terminating the arterial lumen, short of the tip, including a part of the outer wall tapering inwards to merge with the septum wall, the outside surface of the outer wall being smooth and continuous to offer minimum frictional resistance to insertion into the body of a patient, the inside walls of both lumens being smooth and continuous and the transition of the lumens between the said respective parts being smooth and uninterrupted to facilitate the insertion and removal of obturators into and from the respective lumens to extend from their proximal ends to their distal ends, the outer wall being provided with at least one blood access orifice in the distal end part of the arterial lumen and at least one blood access orifice in the distal end part of the venous lumen, and an obturator extending within each lumen throughout its length to prevent the tubular body from kinking when the catheter is inserted in the body of a living being and removable after insertion whereby the catheter remains in the body unkinked, the obturator in the venous lumen having a central passage for a guidewire extending lengthwise through it.

14. A catheter, as defined in claim 13, in which a single integral venous lumen extends from the body at the distal end to a tip, and the arterial lumen terminates at a predetermined point spaced from the tip, and a hollow obturator protrudes from the end of the venous lumen, and the surface of the tip of the distal end of the venous lumen merges smoothly to the surface of the obturator.

15. A catheter, as defined in claim 13, in which there is an obturator in each lumen made of flexible plastic and of substantially the same cross-sectional shape and size to fit in the lumen in the intermediate part, the obturator in the arterial lumen being solid and the obturator in the venous lumen having a passage extending longitudinally therethrough to receive a metallic guidewire extending through it.

16. A catheter, as defined in claim 13, in which there are obturators having different cross-sections from their respective lumens, whereby after the obturators are assembled in both lumens there is a slight spacing in the vicinity of the junction of the septum wall and the wall of the tubing between the obturator and the tubing wall.

17. A catheter, as defined in claim 13, in which the obturators are plastic rods provided with longitudinal slits to make them more flexible.

18. A catheter, as defined in claim 13, in which the end of each obturator is connected to a male luer lock and the male luer lock is, in turn, connected to a female luer lock connected to an elastic tubing fitting the end of an adapter connected to the end of each lumen, the male luer lock being screwed tightly on the female luer lock so that the obturators bear against the ends of the respective lumens and put the body of the catheter under prestressed tension.

* * * * *